(12) United States Patent
Zemel et al.

(10) Patent No.: US 9,351,790 B2
(45) Date of Patent: May 31, 2016

(54) ELECTRODE GEOMETRIES AND METHOD FOR APPLYING ELECTRIC FIELD TREATMENT TO PARTS OF THE BODY

(71) Applicant: M.O.E. MEDICAL DEVICES LLC, New Rochelle, NY (US)

(72) Inventors: Marc I. Zemel, New Rochelle, NY (US); Gennady Friedman, Richboro, PA (US)

(73) Assignee: M.O.E. MEDICAL DEVICES LLC, New Rochelle, NY (US)

( * ) Notice: Subject to any disclaimer, the term of this patent is extended or adjusted under 35 U.S.C. 154(b) by 0 days.

(21) Appl. No.: 14/584,357

(22) Filed: Dec. 29, 2014

(65) Prior Publication Data

US 2015/0182282 A1 Jul. 2, 2015

Related U.S. Application Data

(60) Provisional application No. 61/921,304, filed on Dec. 27, 2013.

(51) Int. Cl.
*A61B 18/14* (2006.01)
*A61B 18/04* (2006.01)
*A61B 18/12* (2006.01)
*A61B 18/00* (2006.01)

(52) U.S. Cl.
CPC .......... *A61B 18/1492* (2013.01); *A61B 18/042* (2013.01); *A61B 18/1206* (2013.01); *A61B 2018/0022* (2013.01); *A61B 2018/00267* (2013.01); *A61B 2018/00577* (2013.01); *A61B 2018/00595* (2013.01); *A61B 2018/00613* (2013.01); *A61B 2018/122* (2013.01)

(58) Field of Classification Search
None
See application file for complete search history.

(56) References Cited

U.S. PATENT DOCUMENTS

| | | | |
|---|---|---|---|
| 4,672,951 A | 6/1987 | Welch | |
| 4,906,576 A * | 3/1990 | Marshall, III | B01D 57/02 435/173.6 |
| 4,946,793 A * | 8/1990 | Marshall, III | B01D 57/02 435/173.6 |
| 5,318,525 A | 6/1994 | West et al. | |
| 5,431,649 A | 7/1995 | Mulier et al. | |
| 5,480,382 A | 1/1996 | Hammerslag et al. | |
| 6,043,066 A * | 3/2000 | Mangano | C12M 35/02 435/173.1 |
| 6,585,718 B2 | 7/2003 | Hayzelden et al. | |

(Continued)

FOREIGN PATENT DOCUMENTS

| | | |
|---|---|---|
| AU | 2006239843 A1 | 11/2006 |
| AU | 2006279395 A1 | 2/2007 |

(Continued)

OTHER PUBLICATIONS

European Search Report in related European application No. EP12741722, mailed Aug. 25, 2014.

(Continued)

*Primary Examiner* — Kennedy Schaetzle
(74) *Attorney, Agent, or Firm* — Brian R. Pollack; Day Pitney LLP

(57) ABSTRACT

The present disclosure provides a variety of systems and techniques for generating and applying plasmas and/or electric fields alone, or in combination with other therapies, to living tissue to treat different tissue conditions as well as other conditions, such as tumors, bacterial infections and the like while limiting electrical current generation within said tissue.

22 Claims, 26 Drawing Sheets

(56) References Cited

U.S. PATENT DOCUMENTS

| | | | |
|---|---|---|---|
| 6,846,290 B2 | 1/2005 | Lizzi et al. | |
| 6,961,620 B2 | 11/2005 | Rioux et al. | |
| 7,850,685 B2 | 12/2010 | Kunis et al. | |
| 8,394,091 B2 | 3/2013 | Rioux et al. | |
| 8,419,681 B2 | 4/2013 | Sell | |
| 8,486,062 B2 | 7/2013 | Belhe et al. | |
| 8,535,303 B2 | 9/2013 | Avitall et al. | |
| 8,583,260 B2 | 11/2013 | Knudson | |
| 9,005,188 B2 | 4/2015 | Wandke et al. | |
| 2002/0010491 A1* | 1/2002 | Schoenbach | A61B 18/1206 607/2 |
| 2003/0170898 A1* | 9/2003 | Gundersen | A61N 1/327 435/461 |
| 2005/0021016 A1 | 1/2005 | Malecki et al. | |
| 2005/0038375 A1 | 2/2005 | Nitzan et al. | |
| 2006/0134031 A1 | 6/2006 | Decola et al. | |
| 2006/0189976 A1 | 8/2006 | Karni et al. | |
| 2006/0269531 A1* | 11/2006 | Beebe | A61N 1/0412 424/93.21 |
| 2007/0239156 A1 | 10/2007 | Palanker et al. | |
| 2008/0045879 A1 | 2/2008 | Prausnitz et al. | |
| 2008/0231337 A1* | 9/2008 | Krishnaswamy | A61N 1/0412 327/291 |
| 2009/0125022 A1 | 5/2009 | Saadat et al. | |
| 2010/0145253 A1 | 6/2010 | Gutsol et al. | |
| 2011/0118719 A1 | 5/2011 | Vissy et al. | |
| 2012/0259270 A1 | 10/2012 | Wandke et al. | |
| 2013/0041443 A1* | 2/2013 | Weissberg | A61N 1/0502 607/115 |
| 2013/0184702 A1 | 7/2013 | Neal et al. | |
| 2013/0261389 A1 | 10/2013 | Long | |
| 2013/0310731 A1 | 11/2013 | Gutsol et al. | |
| 2015/0182282 A1* | 7/2015 | Zemel | A61B 18/1492 606/41 |

FOREIGN PATENT DOCUMENTS

| | | |
|---|---|---|
| CA | 2605650 A1 | 11/2006 |
| CA | 2620294 A1 | 2/2007 |
| CA | 2573522 A1 | 7/2007 |
| EP | 1755733 A2 | 2/2007 |
| EP | 1810626 A2 | 7/2007 |
| EP | 1876986 A2 | 1/2008 |
| EP | 1924698 A2 | 5/2008 |
| IL | 180519 A | 2/2014 |
| JP | 10286316 A | 10/1998 |
| JP | 2008539007 A | 11/2008 |
| JP | 2009507780 A | 2/2009 |
| WO | 2006004595 A2 | 1/2006 |
| WO | 2006116252 A2 | 11/2006 |
| WO | 2007022403 A2 | 2/2007 |
| WO | 2012106735 A2 | 8/2012 |
| WO | 2013040542 A1 | 3/2013 |
| WO | 2013130655 A1 | 9/2013 |

OTHER PUBLICATIONS

International Search report in related International application No. PCT/US2012/055726, mailed Dec. 27, 2012.

International Preliminary Report on Patentability and Written Opinion in related International application No. PCT/US2012/055726, issued Mar. 18, 2014.

International Preliminary Report on Patentability and Written opinion in related International application No. PCT/US2012/031923, issued Aug. 6, 2013.

International Search report in related International application No. PCT/US2012/031923, mailed Jul. 12, 2012.

European Supplementary Search Report, EPO's Opinion and Transmitting Communication in related European patent application No. EP 12831818, Apr. 7, 2015.

International Search Report and Written Opinion in related International application No. PCT/US2014/072532, Mar. 12, 2015.

USPTO Non-Final Office Action in related U.S. Appl. No. 13/943,012, Nov. 20, 2014.

USPTO's Notice of Allowance issued in related U.S. Appl. No. 13/943,012, Aug. 3, 2015.

* cited by examiner

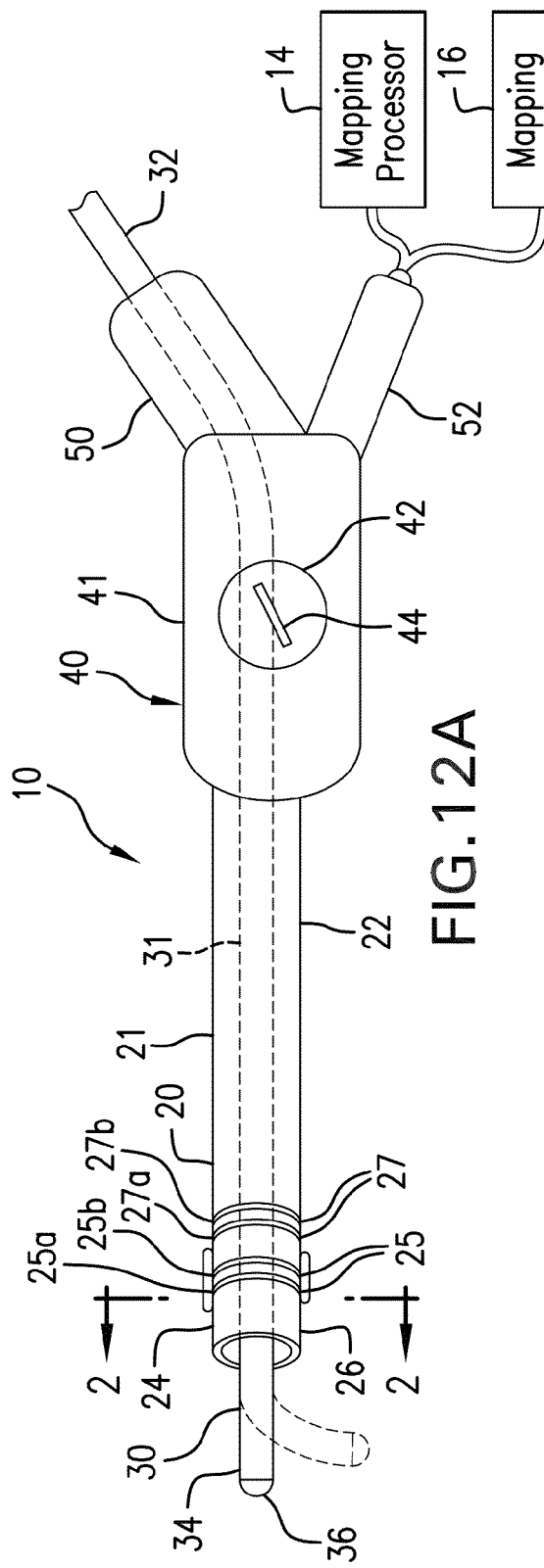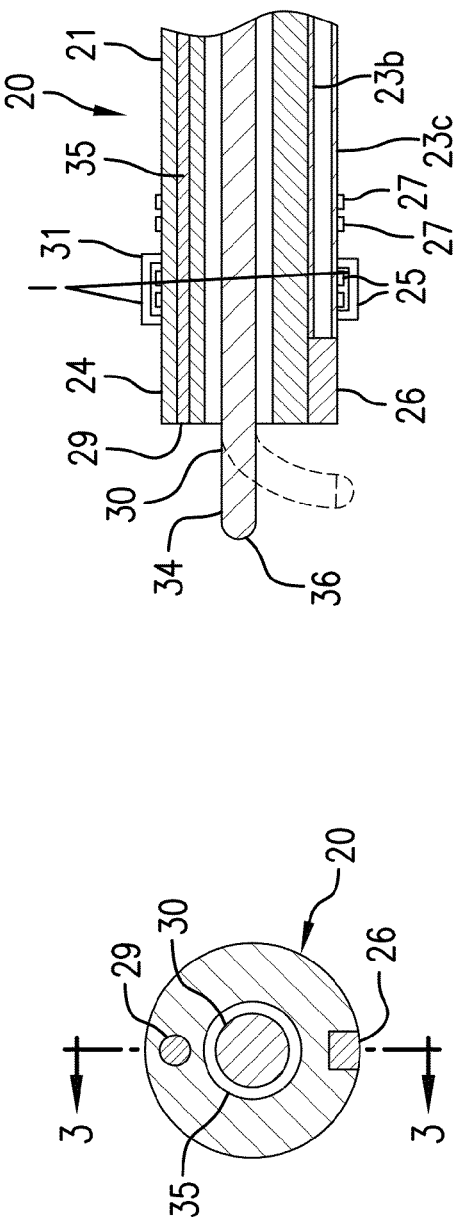

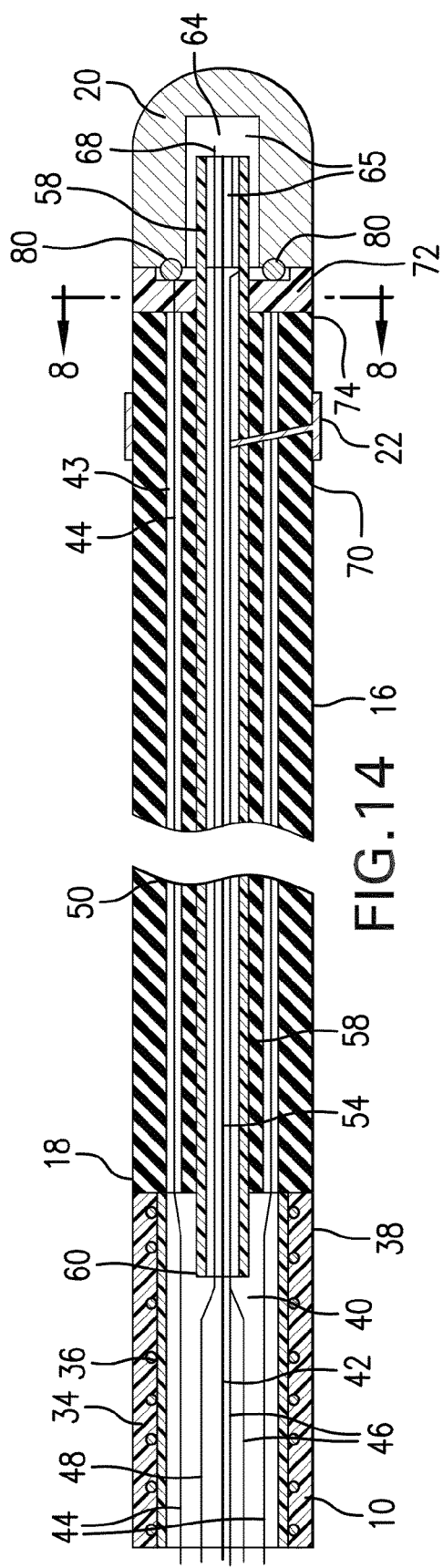

US 9,351,790 B2

ELECTRODE GEOMETRIES AND METHOD FOR APPLYING ELECTRIC FIELD TREATMENT TO PARTS OF THE BODY

CROSS-REFERENCE TO RELATED APPLICATIONS

This application claims the benefit of priority to U.S. Provisional Patent Application Ser. No. 61/921,304, filed Dec. 27, 2013. This patent application is related to International Application No. PCT/US2012/55726, filed Sep. 17, 2012, which in turn claims the benefit of priority to and is a continuation-in-part of International Application No. PCT/US2012/31923, filed Apr. 2, 2012. This application is related to International Application No. PCT/US2012/55726, filed Sep. 17, 2012, which in turn claims the benefit of priority to U.S. Provisional Patent Application Ser. No. 61/535,986, filed Sep. 17, 2011 and U.S. Provisional Patent Application Ser. No. 61/584,399, filed Jan. 9, 2012. This application is also related to U.S. patent application Ser. No. 14/215,214, filed Mar. 17, 2014 which in turn claims the benefit of priority to U.S. Provisional Application Ser. No. 61/803,775, filed Mar. 20, 2013 and U.S. Provisional Application Ser. No. 61/803,776, filed Mar. 20, 2013. The disclosure of each of the aforementioned patent applications is incorporated by reference herein in its entirety for any purpose whatsoever.

BACKGROUND

1. Field of the Disclosure

The present disclosure relates to methods and systems for treating various tissue disorders. Particularly, the present disclosure is directed to the treatment of tissue using the application of strong electric fields, among other things.

2. Description of Related Art

For some time now people practicing medicine have been applying electric fields to living tissue in various ways. The present disclosure improves on the state of the art.

SUMMARY OF THE DISCLOSURE

The purpose and advantages of the present disclosure will be set forth in and become apparent from the description that follows. Additional advantages of the disclosed embodiments will be realized and attained by the methods and systems particularly pointed out in the written description hereof, as well as from the appended drawings.

Of known techniques for applying electrical fields to tissue, most of these different types of electric field applications in medicine can be categorized as 1) thermal and 2) non-thermal.

Applicant has appreciated that most thermal electric field applications increase the temperature of target tissue significantly to cause tissue death typically through processes of necrosis, and eventual ablation and cauterization. Applicant has observed that such processes affect not only cells in tissues, but to a very significant extent extracellular tissue matrix including various biological fibers. They also have poor discrimination between different cells and extracellular materials. Many proteins in the affected tissues are denatured through temperature increase.

Electric field causing increase of temperature in target tissues can be applied in a number of different ways and may differ in various parameters. Some have frequency in radio and even microwave ranges (1 MHz-300 MHz). Applications where electric fields in this frequency range are applied that have sufficient intensity and duration to cause tissue heating of more than 40 degrees Celsius above normal body temperature for a time exceeding a few seconds are usually referred to as RF or microwave ablation. RF and microwave hyperthermia are applications where the target tissue temperature is raised by about 5-10 degrees for a period of minutes. Intense tissue heating and cauterization has also been accomplished by electric field through conduction of relatively low frequency current through tissues. In some cases, such as when a Bovie knife is used in surgery, an ionized gas referred to as plasma can form between the target tissue and an electrode supplying the current. In thermal treatments, penetration of the field and heat generated by it into tissues depends strongly on the details of the kinetics of heat diffusion and tissue modification processes. As a result, the depth of the thermal effect will depend strongly on the power density as well as time.

Wider use of non-thermal electric field effects in medicine are probably more recent, although non-thermal effects have been known since the time of Volta and Galvani who used the electric field to create excitation of nerve tissue and muscle contraction. It appears that today non-thermal applications of the electric field include nerve, muscle and brain stimulation, stimulation of wound and bone healing, pain management, genetic modification and anti-cancer therapy. The key feature of non-thermal applications of electric field in medicine is that their effects can be different for different types of cells and tissues.

For example, electric field when directed along nerve fibers, having a magnitude of around 0.5-5 V/cm and a pulse duration of several microseconds is known to have an effect on excitation of action potential in nerve and muscle fibers, while also having no immediately noticeable effects on other cells and tissues. Stimulation of nerve and muscle tissue has most often employed exposed implantable conducting electrodes (e.g., as with pacemaker devices from Medtronic, Inc.), conduction of current through skin (transcutaneous electric nerve stimulation or TENS) and magnetic field pulses that induce electric fields in nerve tissues as in the case of transcranial magnetic stimulation ("TMS", described, for example, in U.S. Pat. No. 4,672,951, which is incorporated by reference herein in its entirety for any purpose whatsoever).

More recently, alternating electric fields of around 1V/cm in magnitude, with the frequency range of around 100-200 KHz and many hours of exposure (around 24 hours) have been shown to interfere with proliferation of cells (Eilon D. Kirson et. al., PNAS, vol. 104 no. 24, pp. 10152-10157). This has been used, for example, as the basis for glioblastoma (a type of brain cancer) treatment developed by the Novocure Inc. where electrodes are placed on skin of the head and voltage of up to a few volts are applied at frequencies between 50-300 KHz to create fields of around 1V/cm within the target area in the brain.

Electric field pulses lasting from few microseconds to milliseconds and producing around 200-1000 mV across cellular membranes (they are typically around 5 nanometers thick) are known to cause an electroporation effect believed to create pores in cellular plasma membranes. Electroporation has been used for decades in cell cultures to transfer various molecules including DNA into cells, often for the purposes of transfection and subsequent genetic modification. The electroporation effect is known to depend in complex ways on the field magnitude, pulse repetition frequency and the overall number of pulses. When pulse frequency, duration or number becomes sufficiently large, the cells die often through the mechanism of apoptosis.

Electroporative treatment that leads to cell death is known as irreversible electroporation effect ("IRE"). More recently, electroporation has been employed in medicine not only to modify cells in vitro, but to treat tissues within human and animal bodies. Examples of such applications include a treatment by a device called the Nanoknife™ device by Angiodynamics Corp. wherein exposed solid conducting electrodes are inserted into the target tissue such as a tumor or an enlarged prostate and pulses of voltage between the electrodes generate conduction current that produce electric field between the electrodes. In typical situations, electroporation electrodes are separated by a 1-5 cm gap and voltages of 100-2000 Volts are applied. Electroporative treatment has also been proposed and used in medical applications to assist in the uptake of chemotherapeutic agents.

Recent advances in electroporation include reduction of voltage pulse length as well as the pulse rise and fall times. Faster voltage application processes permit greater penetration of the electric field into cells because it does not allow the time for the currents through the cell membrane to screen the applied field. Yet, the delivery of intense electric fields with uninsulated electrodes as described above can cause local tissue necrosis (via heat) and electrolysis, leading to excessive damage and scar formation near the electrodes. So-called non-thermal irreversible electroporation (IRE or NTIRE) is possible with bare electrodes, but is severely limited in field strength and pulse repetition rate [Davalos 2012]. The practical limits are approximately 100 pulses at 1 Hz repetition rate with field strengths of 1000 to 2000 V/cm and pulse widths of 50 to 100 microseconds. These treatment parameters lead to very long treatment times and/or limited treatment areas.

Another example of non-thermal electric field treatment is one where pulses of radio or microwave frequency electromagnetic field are applied to cells and tissues in the body. The intensity of the electric field in such treatments is similar to the intensity employed to heat the tissue. However, by making pulses shorter than milliseconds and by limiting the pulse repetition frequency, the heating effect can be avoided. Such applications of non-thermal electric field treatment have primarily been applied in wound care and have been suggested to help wounds heal faster. As an example, such treatments have been reported using the Diapulse™ device wherein electromagnetic field in the frequency range of 25-30 MHz is pulsed at rates of 10-800 pulses per second with each pulse lasting usually less than 100 microseconds (see for example Wound Care: A Collaborative Practice Manual for Health Professionals, by Carrie Sussman and Barbara Bates-Jensen, Kluwer Health, pp. 580-583). Faster pulse rates or longer pulses seem to result in tissue heating. The field is applied to tissue by coupling the pulsed electromagnetic field generators to a waveguide, which may be terminated by an antenna. No contact between the tissue and the antenna is necessary, although placement of the antenna in close proximity to the target tissue may be desirable.

In some cases electric fields within tissues can be created without the need for the conduction current to flow from the electrodes into the tissues. This is typically the case for RF and microwave based electromagnetic field treatments. It is also the case when pulsed magnetic fields are employed to induce electric field in tissue. In such cases the electric field magnitude within tissue is usually relatively weak and treatments often require long-term (hours) field exposure.

In other cases, particularly those requiring relatively low frequency, long (more than one second) pulse length or large magnitude electric field, current through the exposed conducting electrode is directed through tissue to another electrode. When the required field and the required conduction current are relatively small, electrochemical processes occur in the vicinity of the exposed conducting electrodes with a relatively low intensity. More intense currents producing more intense electric fields, like those that are often required in electroporation treatments with microsecond-long pulses, may result in significantly more intense electrochemical processes and heat generation near the electrodes. This can cause significant unwanted tissue damage near the electrodes, which can be particularly troublesome when one wants to perform highly localized tissue treatment without substantial heating anywhere or to control heating effects separately. Some examples of medical applications where such effects are highly undesirable include treatment of brain tissues and treatment of thin tissue layers near tissue walls such as those found within or around blood vessels, cardiac chambers, intestinal cavities, the esophagus, colorectal passages, bronchial tubes, urological passageways, nasal passages, and skin. Pulses of electric field lasting microseconds also can excite nerves and muscles. This could potentially be avoided by employing nanosecond long pulses, particularly if the direction of the electric field is perpendicular to the direction of the nerve fibers. However, currents passed between electrodes in tissue will remain problematic.

It is an objective of this disclosure to provide systems and methods for applying intense electric fields within tissues without the use of conduction current or conduction current carrying electrodes in order to avoid generation of heat and/or gas bubbles near the electrodes that might occur due to electrochemical processes on the electrodes that are driven by the conduction currents.

In some embodiments, the disclosure provides a system for treating a region of living tissue, including an electrical signal generator configured to generate a time-varying electric field having a plurality of pulses, each of said plurality of pulses having rise and fall time lasting between about 1-100 microseconds and lasting for a duration between about 2-200 microseconds. The system can further include at least one electrode configured to be placed proximate an anatomical region of interest to deliver the time varying electric field to the anatomical region of interest. The electric field can have a peak magnitude between about of 100-100,000 V/cm. The peak value of the electric field within tissue at the anatomical region of interest can be controlled by the rate of voltage variation and by the peak voltage imposed by the electrical signal generator. The system can further include an electrical current limiting barrier layer configured to be disposed between the at least one electrode and the anatomical region of interest.

The disclosure also provides embodiments of a system for treating a region of living tissue, including an electrical signal generator configured to generate a time-varying electric field having a plurality of pulses, each of said plurality of pulses having rise and fall time lasting between about 1-1000 nanoseconds and lasting for a duration between about 2-2000 nanoseconds. The system can further include at least one electrode configured to be placed proximate an anatomical region of interest to deliver the time varying electric field to the anatomical region of interest. The electric field can have a peak magnitude between about 100-100,000 V/cm. The peak value of the electric field within tissue at the anatomical region of interest can be controlled by the rate of voltage variation and by the peak voltage imposed by the electrical signal generator. The system can further include an electrical current limiting barrier layer configured to be disposed between the at least one electrode and the anatomical region of interest.

The electrical current limiting barrier can include one or more of (i) an insulating material between about 1-2000 micrometers in thickness, (ii) a gas filled gap that begins to conduct electrical current therethrough when the electric field across the gas filled gap exceeds the ionization threshold of gas within the gas filled gap, and (iii) an ionic conducting liquid or polymer, among other things. The at least one electrode can be configured to apply an electric field to the anatomical region of interest that is oriented in a direction that is predominantly normal or tangential to the said electrode within the anatomical region of interest, among other orientations. The at least one electrode can be formed proximate a surface of an inflatable member that can be selectively inflated to bring the at least one electrode into proximity of the anatomical region of interest. The at least one electrode can be patterned. The patterning can be defined by alternating regions of exposed conductor and insulating material, or alternating regions of insulating material of differing thicknesses, among other implementations. The at least one electrode can be flexible and/or resilient.

In some implementations, the at least one electrode can include a plurality of elongate conductors surrounding a central axis that can be deployed radially outwardly from the central axis. The plurality of elongate conductors can include an insulating layer along substantially their entire length. The thickness of the insulating layer can change along the length of the plurality of elongate conductors linearly, nonlinearly or in a stepwise fashion. The thickness of the insulating layer can be less along a portion of the plurality of elongate conductors that is configured to be placed proximate the anatomical region of interest. The plurality of elongate conductors can be partially insulated along a portion of the plurality of elongate conductors that is configured to be placed proximate the anatomical region of interest.

The disclosure further provides methods that include applying an electric field to the anatomical region of interest using any system disclosed herein. The anatomical region of interest can be exposed to the electric field for between about one tenth of a second and about one hour, between about five seconds and about twenty minutes, between about thirty seconds and about ten minutes, between about three minutes and about seven minutes, or in any time increment of one second between one second and ten thousand seconds. The anatomical region of interest can be on or in an animal or human.

It is to be understood that both the foregoing general description and the following detailed description are exemplary and are intended to provide further explanation of the embodiments disclosed herein. The accompanying drawings, which are incorporated in and constitute part of this specification, are included to illustrate and provide a further understanding of the methods and systems of the disclosure. Together with the description, the drawings serve to explain the principles of the disclosed embodiments.

BRIEF DESCRIPTION OF THE DRAWINGS

FIGS. 10A-10C illustrate further embodiments of an electrode probe in accordance with the disclosure, wherein FIG. 10A illustrates an elongate insulated electrode with a concave treatment tip, FIG. 10B illustrates a cross section of the embodiment of FIG. 10A, and further wherein FIG. 10C illustrates a variation of the electrode of FIG. 10A wherein the concave treatment tip is on a side of the probe.

FIG. 12A is a perspective view of a first embodiment of a magnetically assisted steering catheter system; FIG. 12B is a cross-sectional detail of a distal end of the system of FIG. 12A, showing a guidewire inserted through the system; and FIG. 12C is a cross-section of the system of FIG. 12B, taken along line 3-3.

FIG. 14 is a front cross-sectional view of the distal tip of a further device in accordance with the disclosure.

DETAILED DESCRIPTION

Reference will now be made in detail to the present preferred embodiments of the disclosure, examples of which are illustrated in the accompanying drawings. The methods and corresponding steps of the disclosed embodiments will be described in conjunction with the detailed description of the exemplary systems.

Significant challenges facing the use of electric fields in medicine are related to the control of magnitude, rise and fall time, duration and time waveform of electric field pulses and depth of penetration of the electric field into the tissue, while also avoiding conduction current associated thermal and electrochemical effects near the electrode. A simplified model will be used here to describe some of the methods by which these electric field parameters can be controlled.

Figure 1:
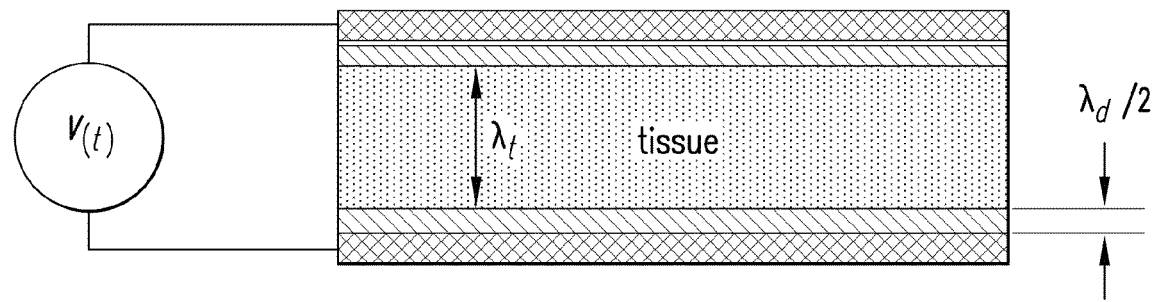
FIG. 1 is a schematic showing an exemplary geometrically simplified model for calculation of electric field generation in tissue.

In this simplified model, illustrated in FIG. 1, a layer of tissue is positioned between two conducting electrodes. Placing a separation layer or layers of dielectric insulating material, resistive, semiconducting or other material between the tissue and the electrodes may be employed to 1) prevent or limit conduction of current through the tissue and heating or chemical processes associated with such conduction; 2) permit to create conformal contact between an irregularly shaped tissue surface and the surface of an electric field controlling device. Besides solid insulating material, one may use semiconducting materials that may permit control of electric field penetration via thermal heating or optical excitation. One may also use liquid, cream or gel-type insulating, conducting or semiconducting materials that permit conformation to the irregular tissue surface. Such liquids, creams, or gels can be applied to the target treatment surface via a suitable applicator, such as manual application, sprays, injection, irrigation, and the like. One may even use gas or ionized gas material (plasma) as the separation layer between tissue and conducting solid electrode. These materials can also be used in any combination of two three, four, and so on.

The effect of the electrode geometry on the field parameters will not be considered in this simplified model. Rather, this will be discussed later. Instead, the electrodes, separating materials and tissue will be assumed to have planar interfaces and extended infinitely within the interfacial plane. This effectively permits the field normal to the material interfaces to change only at the material interfaces. Combined thickness of the dielectric insulator is denoted as $\lambda_d$, while thickness of the tissue is denoted as $\lambda_t$.

Materials in this model will be described by parameters of relative dielectric permittivity k and conductivity σ. Relative dielectric permittivity is the ratio of the dielectric permittivity of the material $\in$ to the dielectric permittivity of vacuum $\in_0 \approx 10^{-11}$ Farads/m. Conductivity is the coefficient of proportionality between the effective conduction current density responsible for energy dissipation into heat and the electric field.

In the discussion below, for the sake of simplicity, conductivity of the separation layers positioned between the conducting electrodes and tissue will be assumed to be zero, while the frequency independent relative dielectric constant $k_d$ of this dielectric material may have the magnitude varying from about 2 to 10 (or any increment of 0.1 therebetween) for different practical materials. In general, conductivity of the separation layer will contribute to energy dissipation into heat and to slower response to the applied voltage. Electrical conductivity of tissues can vary significantly depending on cell density, cell type and water content. However, for most tissues it remains below 1 S/m at frequencies below 1 GHz. Relative dielectric permitivities of tissues may also vary significantly. They are often quite large ($10^3$-$10^7$) at frequencies below about the so-called α—dispersion frequency which is typically around $10^4$-$10^6$ Hz, falling to about $10^2$ (relatively permittivity of water) at the β—dispersion frequency which is typically around $10^7$-$10^8$ Hz and then decreasing below $10^2$ at frequencies higher than the γ—dispersion frequency which is around $10^{10}$ Hz.

Figure 2:
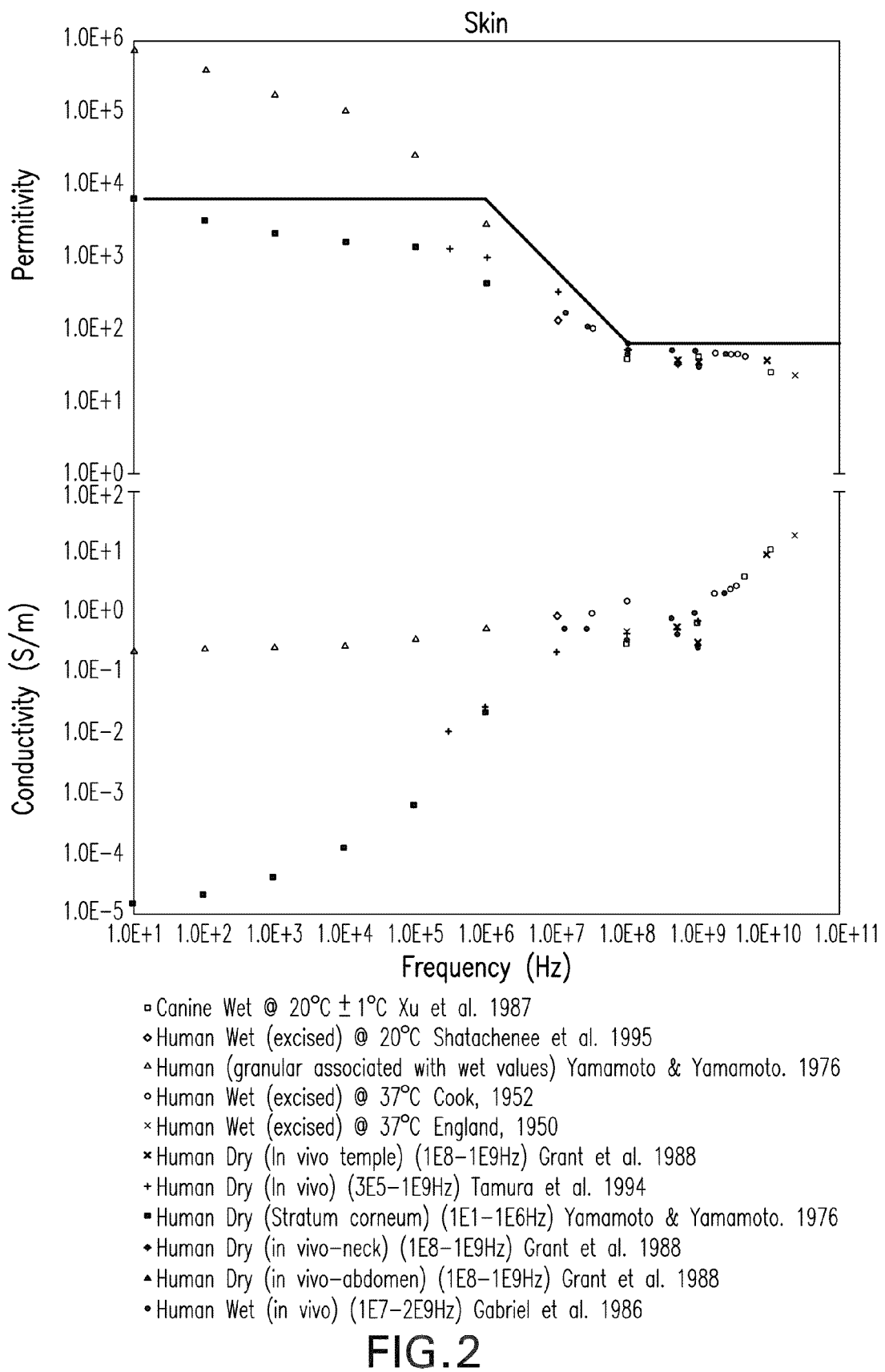
FIG. 2 is a schematic showing typical frequency response of relative dielectric permittivity and conductivity of skin tissue to electric field.

As an example, if we consider skin as the target tissue, the relative dielectric permittivity $k_t$ and conductivity $\sigma_t$ is given in FIG. 2 (data gathered from a number of sources and reviewed by C. Gabriel, S. Gabriel and E. Corthout published in Phys. Med. Biol. 41 (1996) 2231-2249) as a function of frequency.

Figure 3:
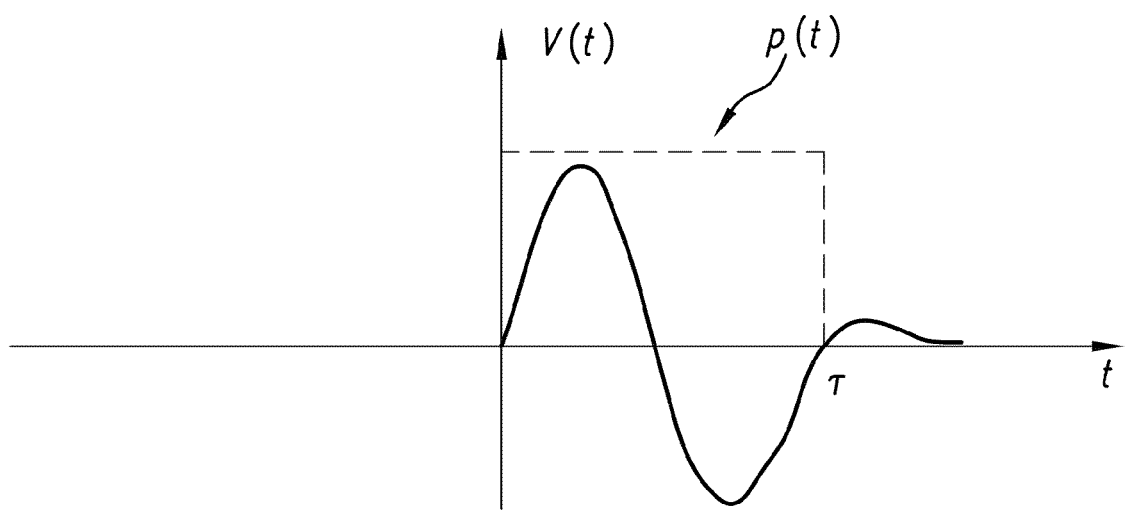
FIG. 3 is a schematic of a typical voltage pulse shape.

A typical time-dependent waveform of voltage applied to an electrode may have the shape similar to one shown in FIG. 3. It can be interpreted as a pulse because it can usually be represented as a product of an oscillating function such as a sinusoidal function $\sin(2\pi f_0 t)$ wherein $f_0$ is the oscillation frequency, and a function like a rectangular pulse $$p(t) = \begin{cases} V_{max}, & 0 \le t < \tau = \dfrac{R}{f_0} \\ 0, & \text{otherwise} \end{cases} \tag{1a}$$

wherein R is the number of oscillation periods within the pulse. This number can be less than 1 when less than one oscillation period occurs within the pulse. Thus, a simplified model of voltage pulse may be:

$$V(t) = p(t)\sin(2\pi f_0 t) \tag{1b}$$

It is often convenient to use Fourier transformed variables called phasors in place of time varying functions in mathematical models of linear systems. Fourier transform of the above pulse can accordingly be written as:

$$\tilde{V}(f) = V_{max}\tau \cdot \operatorname{sinc}(\tau(f - f_0)) = V_{max}\frac{R}{f_0}\operatorname{sinc}\left(R\frac{(f - f_0)}{f_0}\right) \tag{2a}$$

where $$\operatorname{sinc}(x) = \frac{\sin(x)}{x} \tag{2b}$$

The Fourier transformation of the typical pulse illustrates that, in the phasor representation, the center frequency of the pulse is the oscillation frequency $f_0$, while the bandwith of frequencies associated with the pulse spans the range of about $\Delta f = 2\pi/\tau = 2\pi f_0/R$. This justifies the use of phasors at frequencies of around $1/\tau$ for pulses of approximate duration $\tau$.

In the various cases considered below the tissue conductivity will be assumed to be constant and have a value of around 1 S/m at all frequencies of interest, while the relative permittivity of the tissue will be taken to be consistent with the following relationship between electric field displacement $\tilde{D}_t$ and the electric field $\tilde{E}_t$ phasors:

$$\tilde{D}_t = \epsilon_0 k_{t0} \frac{1 + j2\pi\dfrac{f}{f_\beta}}{1 + j2\pi\dfrac{f}{f_\alpha}} \tilde{E}_t = \epsilon_0 k_0(f)\tilde{E}_t \tag{3}$$

where $j=\sqrt{-1}$, f is the electric field phasor frequency, $k_{t0}=10^4$ is the relatively dielectric permittivity of tissue at frequencies below the α—dispersion frequency $f_\alpha=10^6$ Hz and where $f_\beta=10^8$ is the β—dispersion frequency. An asymptotic Bode plot of the above relationship is superimposed on the actual data in FIG. 2 as a solid black line to illustrate how well this relationship approximates the data found in the literature. Phasor relationship may be converted to the relationships between actual time dependent quantities by using time differentiation in place of multiplication by $j2\pi f$ and the time dependent quantity itself in place of the phasor.

Boundary conditions between the tissue and the dielectric insulator provide the following relationship between phasors of fields in the dielectric insulator and tissue:

$$\epsilon_0 j2\pi f(k_d\tilde{E}_d - k_t(f)\tilde{E}_t) = \sigma_t\tilde{E}_t \tag{4}$$

$$\tilde{E}_d\lambda_d + \tilde{E}_t\lambda_t = \tilde{V} \tag{5}$$

Finding $\tilde{E}_d$ from (5) and $k_t(f)$ from (3) and substituting them into (4) yields:

$$j2\pi f\frac{\epsilon_0 k_d}{\sigma_t}\frac{1}{\lambda_d}\tilde{V} = \left(1 + j2\pi f\frac{\epsilon_0 k_{t0}}{\sigma_t}\frac{1 + j2\pi\dfrac{f}{f_\beta}}{1 + j2\pi\dfrac{f}{f_\alpha}} + j2\pi f\frac{\epsilon_0 k_d}{\sigma_t}\frac{\lambda_t}{\lambda_d}\right)\tilde{E}_t \tag{6}$$

Let $$\frac{\epsilon_0 k_d}{\sigma_t} = \tau_d, \quad \frac{\sigma_t}{\epsilon_0 k_d} = f_d, \quad \frac{\epsilon_0 k_{t0}}{\sigma_t} = \tau_t, \quad \frac{\sigma_t}{\epsilon_0 k_t} = f_t \tag{7a}$$

Using numbers typical for wet skin given above and assuming an intermediate value of the dielectric insulator relative permittivity $k_d=5$, $$f_d = \frac{1}{10^{-11} \times 5} = 2 \times 10^{10} \text{ Hz}, f_t = \frac{1}{10^{-11} \times 10^4} = 10^7 \text{ Hz} \quad (7b)$$

Equation (6) makes it clear that, if the voltage V varies in time very slowly and the frequency f is near zero, no electric field will exist within the tissue. This is a fundamental property of the system in which no conduction current is permitted to pass from electrodes into tissues. Electric field can be maintained within tissue for a long period of time if the conduction current can be passed from the electrodes through the tissue. However, equation (6) illustrates that, as the frequency increases, electric field can be delivered into the tissue and maintained in it for some time. In this case, characteristic time $\tau_d$ can be interpreted physically as the time it takes for the electric field energy to be transferred from the tissue into the dielectric insulator. Characteristic frequency $f_d$ is the inverse of this time. Characteristic time $\tau_t$ can be viewed as the maximal time of electric field energy dissipation into heat within the tissue and $f_t$ is the inverse of this electric field energy dissipation time. Using these characteristic frequencies equation (6) can be written as:

$$j2\pi \frac{f}{f_d} \frac{1}{\lambda_d} \tilde{V} = \left( 1 + j2\pi \frac{f}{f_t} \frac{1 + j2\pi \frac{f}{f_\beta}}{1 + j2\pi \frac{f}{f_\alpha}} + j2\pi \frac{f}{f_d} \frac{\lambda_t}{\lambda_d} \right) \tilde{E}_t \quad (8)$$

It is now useful to consider a couple of different modes of operation that can be used to deliver electric fields of different magnitudes and durations into the tissue using insulated electrodes.

Mode 1: Microsecond long field pulses, small to intermediate ratio of tissue to dielectric thickness $$\left( \frac{\lambda_t}{\lambda_d} = 10 - 50 \right)$$

The use of voltage pulses that have on the order of 1-10 microsecond long durations implies that the frequency of operation is around f=0.1-1 MHz. In this case:

$$\frac{f}{f_\beta} = 10^{-3} - 10^{-2}, \frac{f}{f_\alpha} = 10^{-1} - 1, \quad (9)$$

$$\frac{f}{f_d} = 0.5 \times (10^{-6} - 10^{-5}),$$

$$\frac{f}{f_t} = 10^{-2} - 10^{-1}$$

$$\left| 1 + j2\pi \frac{f}{f_t} \frac{1 + j2\pi \frac{f}{f_\beta}}{1 + j2\pi \frac{f}{f_\alpha}} + j2\pi \frac{f}{f_d} \frac{\lambda_t}{\lambda_d} \right| \approx 1 \quad (10)$$

$$j2\pi \frac{f}{f_d} \frac{1}{\lambda_d} \tilde{V} \approx \tilde{E}_t \leftrightarrow \frac{1}{f_d \lambda_d} \frac{dV(t)}{dt} = E_t(t) \quad (11)$$

The above equation illustrates that, in the microsecond pulse mode of operation, the field within tissue is proportional to the rate of change of the voltage applied between the electrodes, rather than the voltage itself. If we take tissue thickness to be around 1 cm, dielectric insulator thickness to be around $\lambda_d$=200 micrometers $$\left( \frac{\lambda_t}{\lambda_d} = 50 \right),$$

and voltage magnitude to be around 10 kV and assume pulse lengths in the range of 1 to 10 microseconds, we find $$|\tilde{E}_t| \approx 1.5 - 15 \left( \frac{V}{cm} \right) \quad (12)$$

These electric fields can be further increased to about 45 V/cm by reducing the thickness of the dielectric insulator to about 100 micrometers and increasing the peak voltage to about 20 kV. It is interesting that, according to equation (11), the field within tissue in virtually independent of tissue's dielectric permittivity in this mode. This could be an advantage in some circumstances when tissues being subjected to electroporation have highly inhomogeneous dielectric permittivity, but when one still wants to apply the same field throughout.

Mode 2: Nanosecond long field pulses, small to intermediate ratio of tissue to dielectric thickness $$\left( \frac{\lambda_t}{\lambda_d} = 10 - 50 \right)$$

The use of voltage pulses that have on the order of 10 nanosecond long durations implies that the frequency of operation is around f=0.1 GHz. In this case:

$$\frac{f}{f_\beta} = 1, \frac{f}{f_\alpha} = 10^2, \frac{f}{f_d} = 0.5 \times 10^{-3}, \frac{f}{f_t} = 10 \quad (13)$$

Substituting the above into (6) one finds that the second term on the right side of (6) is dominant and, as a result, $$\left| 1 + j2\pi \frac{f}{f_t} \frac{1 + j2\pi \frac{f}{f_\beta}}{1 + j2\pi \frac{f}{f_\alpha}} + j2\pi \frac{f}{f_d} \frac{\lambda_t}{\lambda_d} \right| \approx 2\pi \frac{f}{f_t} \frac{f_\alpha}{f_\beta} \quad (14)$$

$$\frac{f_t}{f_d} \frac{f_\beta}{f_\alpha} \frac{1}{\lambda_d} \tilde{V} \approx \tilde{E}_t \leftrightarrow \frac{f_t}{f_d} \frac{f_\beta}{f_\alpha} \frac{1}{\lambda_d} V(t) \approx E_t(t) \quad (15)$$

Dimensionless quantity $$g = \frac{f_t}{f_d} \frac{f_\beta}{f_\alpha} \approx 0.5 \times 10^{-2} \quad (16)$$

can be viewed as an important system parameter that controls the effectiveness of conversion of the applied voltage to the electric field within the tissue in the nanosecond pulsed voltage mode. This quantity will vary in general depending on tissue maximum permittivity, values of various critical tissue dispersion frequencies, tissue conductivity as well as permittivity of the dielectric insulator. Thus, equation (15) demonstrates that, in the nanosecond mode, electric field within tissue is sensitive to all of the tissue's electrical properties in contrast to the microsecond mode of operation when it is sensitive only to the tissue conductivity. This also demonstrates that, by selecting appropriate voltage pulse parameters, it is possible to make more or less tissue selective electric field penetration.

Equation (15) above demonstrates that the electric field within tissue in this mode of operation is more or less independent of the rate of the voltage increase (as long as the increase and decrease of voltage are fast enough to ensure 10 nanosecond pulses). Instead, the field actually increases with the voltage. Physically, this is due to the fact that the conduction current through tissue can be ignored in this mode of operation. If we take the tissue thickness to be around 1 cm, the dielectric insulator thickness to be around $\lambda_d$=200 micrometers $$\left(\frac{\lambda_t}{\lambda_d} = 50\right),$$

and the voltage magnitude to be around 10 kV, we find $$|\tilde{E}_t| \approx 2.5 \times 10^3 \left(\frac{V}{cm}\right) \quad (17)$$

Therefore, using 10 nanosecond pulses or shorter it is possible to achieve peak field magnitudes that are on the order of electroporation fields, although the duration of the field pulse is about $10^3$-$10^6$ times shorter than typical electroporation pulses. Although such field pulses may not actually electroporate cells within the target tissue, they can be used to affect cell behavior in significant ways. Assuming that the rates of change of the field within tissue correspond to the field magnitude in (14) and assuming that the rate of increase is around 5 nanoseconds (half the pulse length), one obtains field rate of change of $5 \times 10^{11}$ V/(cm·s).

It is important to understand how the electric field contributes to tissue heating and what the limit is of pulse frequency, length and field strength when non-thermal treatment is desired. The time-averaged power density deposition due to the electric field within tissue can be estimated from:

$$P_E = \sigma_t |\tilde{E}_t|^2 \frac{f_p}{f} \quad (18)$$

where $f_p$ is the pulse application frequency. In the nanosecond mode, for example, when the peak field of about $$1 \times 10^3 \left(\frac{V}{cm}\right)$$

is obtained, the time-averaged power deposition is about $$10^{-1} \left(\frac{W}{cm^3}\right),$$

while in the microsecond mode when the peak field is about $$50 \left(\frac{V}{cm}\right)$$

and pulses are applied at the same rate, $$0.25 \times 10^{-1} \left(\frac{W}{cm^3}\right).$$

Both power deposition rates are on the same order of magnitude. To estimate the tissue temperature rise due to such power deposition, one can simplify the problem of heat transfer and ignore heat generation due to metabolic activities and heat removal due to blood perfusion of tissue. With these assumptions, heat can only be conducted away from the region subjected to the electric field. For the sake of simplicity, let us also imagine the situation when the field is generating heat in the center of a spherical tissue volume of about a=1 cm radius. In a steady state, the temperature distribution around the electric field heated spherical volume is given by:

$$T(r) = \frac{1}{3} \frac{P_E a^2}{\xi} \frac{a}{r} + T_{body} \quad (19)$$

where $\xi \approx 0.5$ Wm$^{-1}$K$^{-1}$=50 Wcm$^{-1}$K$^{-1}$. The maximum temperature in this steady state distribution occurs on the surface of the electric field heated spherical volume and is given by:

$$T_{max} = \frac{1}{3} \frac{P_E a^2}{\xi} \quad (20)$$

It is clear that for when time-averaged power deposition due to the electric field is on the order of $$P_E = 10^{-1} \left(\frac{W}{cm^3}\right),$$

the maximum temperature is only a fraction of one degree Kelvin above the normal body temperature. Blood perfusion will reduce this temperature rise further. Therefore, nanosecond and microsecond mode treatments can be considered non-thermal when they are limited to several cubic centimeters of tissue volume.

The above model simplifies the calculation of the electric field within tissue by assuming that electrodes are planar and infinite in their extent. In more realistic situations, electrode geometry can be chosen to limit the depth of field penetration into tissue or its spread along the tissue interfaces by choosing electrodes of appropriate size and by spacing electrodes by appropriate distances.

One of the advantages of creating electric field within tissue while limiting conduction current between the electrodes is that it becomes possible to use only a single electrode and avoid placing a second electrode on or within tissue. This is particularly advantageous when applying fields near the skin surface or near the surfaces of various other tissues including lungs, intestinal tissues, esophageal tissues, peritoneal tissues and other similar tissues. One example where substantial field can be created within tissue without piercing its surface using a single electrode is the embodiment of an insulated patch electrode.

Figure 4:
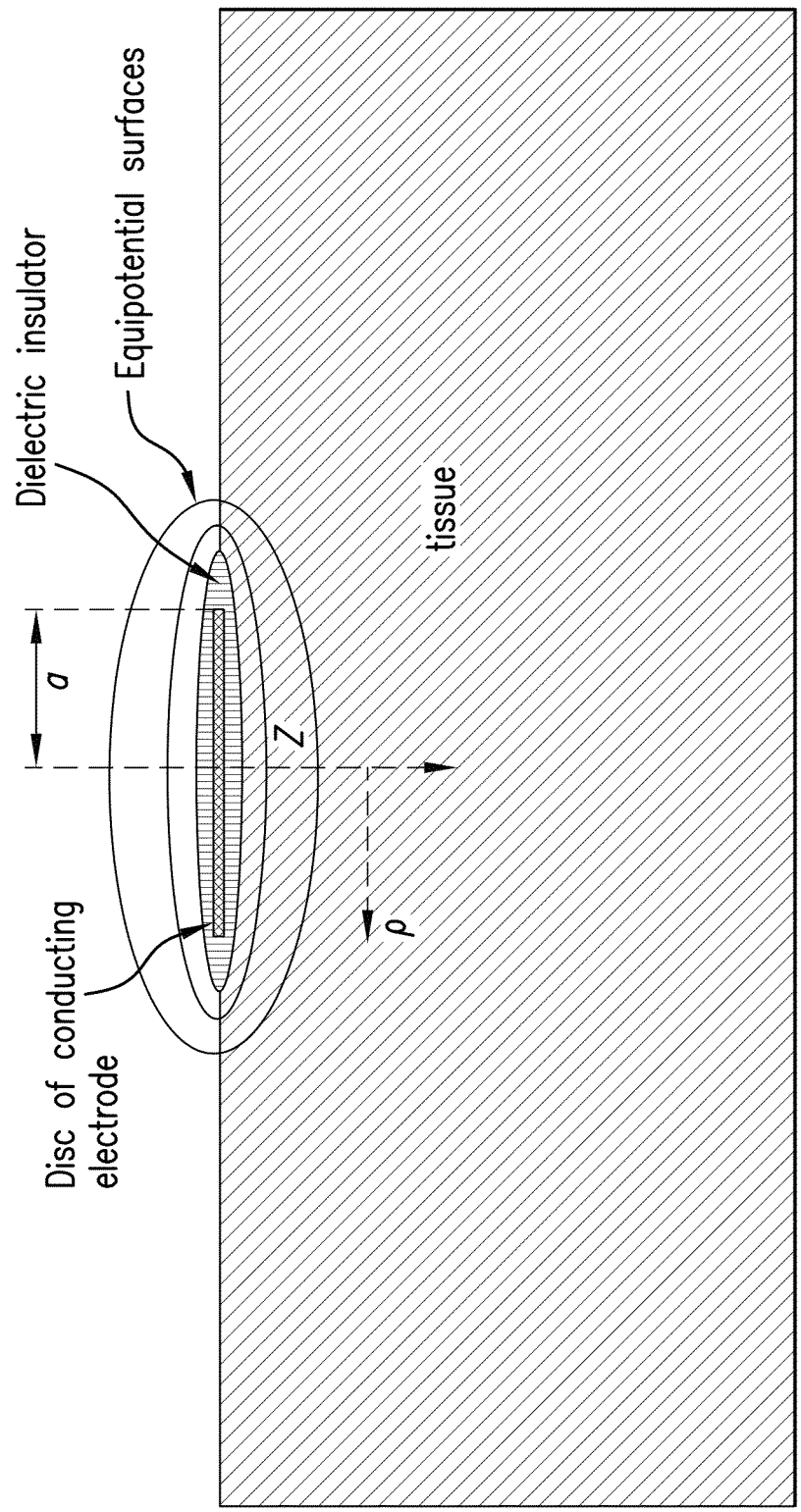
FIG. 4 is a schematic of an exemplary patch electrode.

For the purpose of illustrating the operation of the insulated patch electrode, consider one possible implementation of this embodiment where a thin conductor that can be made of a metal material is surrounded by a thin layer of dielectric insulator and placed on the surface of skin. For the purpose of deriving an analytical approximate model, the thin conductor will be taken to be in the shape of a thin circular disc form and the insulator surrounding it will be taken to have the shape of an oblate spheroid. This is illustrated in FIG. 4 where the cross section of this patch on the surface of tissue is assumed to have a thickness much larger than the dimension of the patch electrode (assumed to be infinite for the purpose of deriving the approximate analytical model).

It can be shown that surfaces of constant potential (equipotential surfaces) form a family of oblate spheroids if the dielectric insulator is also an oblate spheroid whose surface belongs to the same family of equipotential surfaces. If the origin is placed in the center of the conducting disc electrode, while ρ and z denote distances from the axis perpendicular to the disc and along the axis from the origin, respectively (see FIG. 4), the family of the oblate spheroids that are equipotential are given by:

$$\frac{\rho^2}{a^2\cosh^2\eta} + \frac{z^2}{a^2\sinh^2\eta} = 1 \quad (21)$$

where a is the radius of the disc and variable η describes each surface such that the surface of the disc corresponds to η=0 and increasing values of η correspond to the increasing size of the oblate spheroid surface. It can be shown from (21) that $$\sinh(\eta) = \sqrt{\left(\frac{\sqrt{(\rho-a)^2+z^2} + \sqrt{(\rho+a)^2+z^2}}{2a}\right)^2 - 1} \quad (22)$$

and that, on the z-axis where ρ=0

$$\sinh(\eta) = \frac{z}{a} \quad (23)$$

It is also known (see for example W. R. Smythe, Static and Dynamic Electricity, 3rd ed. McGraw-Hill, New York, 1968) that in the highly symmetrical case being considered here the potential due to the disc electrode can be expressed in the form:

$$\tilde{\phi}(\eta) = A\cot^{-1}(\sinh(\eta)) + B \quad (24)$$

where $\tilde{\phi}$ denotes the phasor of the time varying potential, while coefficients A and B are chosen to satisfy boundary conditions. These boundary conditions include a) specified value of the potential on the disc electrode; b) continuity of the potential across the interface between tissue and the dielectric insulator; c) discontinuity of the electric field displacement normal to the interface between tissue and the dielectric insulator by the amount of surface charge density; and d) potential going to zero far away from the electrode disc and the dielectric insulator. To find the final solution to the above electrostatic problem, it is convenient to split the solution volume into two: within the dielectric and within tissue. Using (24), the phasor of the potential within the dielectric can be written as:

$$\tilde{\phi}_d(\eta) = A_d\cot^{-1}(\sinh(\eta)) + B_d \quad (25)$$

Using (23), on the disc axis (z-axis), this reduces to:

$$\tilde{\phi}_d(z) = A_d\cot^{-1}\left(\frac{z}{a}\right) + B_d \quad (26)$$

while the phasor of the electric field on the axis can be found from (26) by differentiation:

$$\tilde{E}_d(z) = -\frac{d}{dz}\tilde{\phi}_d(z) = \frac{A_d}{a}\frac{1}{1+\left(\frac{z}{a}\right)^2} \quad (27)$$

In the tissue, the phasor of the potential can be written as:

$$\tilde{\phi}_t(\eta) = A_t\cot^{-1}(\sinh(\eta)) \quad (28)$$

Using (23), on the disc axis (z-axis), this reduces to:

$$\tilde{\phi}_t(z) = A_t\cot^{-1}\left(\frac{z}{a}\right) \quad (29)$$

giving the electric field phasor on the axis as:

$$\tilde{E}_t(z) = -\frac{d}{dz}\tilde{\phi}_t(z) = \frac{A_t}{a}\frac{1}{1+\left(\frac{z}{a}\right)^2} \quad (30)$$

The form of the field expression in tissue automatically satisfies the boundary condition far away from the electrode (potential is goes to zero). Therefore, boundary conditions should yield the three remaining coefficients: $A_d$, $B_d$ and $A_t$. Taking the thickness of the dielectric on the axis to be $\lambda_d$, the boundary condition of potential continuity is found to be:

$$A_t\cot^{-1}\left(\frac{\lambda_d}{a}\right) = A_d\cot^{-1}\left(\frac{\lambda_d}{a}\right) + B_d \quad (31)$$

The boundary condition on the electric field displacement at the interface between tissue and the dielectric is the same as condition (4) and can be written in this case as:

$$\epsilon_0 j2\pi f(k_d\tilde{E}_d(\lambda_d) - k_t(f)\tilde{E}_t(\lambda_d)) = \sigma_t\tilde{E}_t(\lambda_d) \quad (32)$$

Using the above one finds:

$$\frac{A_d}{A_t} = \frac{(\epsilon_0 j2\pi f k_t(f) + \sigma_t)}{\epsilon_0 j2\pi f k_d} = k(f) \quad (33)$$

Finally, the boundary condition for the specified phasor potential $\tilde{V}$ on the disc conductor is:

$$\tilde{V} = \frac{\pi}{2}A_d + B_d \quad (34)$$

Putting all the boundary conditions together, one finds $$A_t = \frac{\tilde{V}}{\left(\left(\frac{\pi}{2} - \cot^{-1}\left(\frac{\lambda_d}{a}\right)\right)k(f) + \cot^{-1}\left(\frac{\lambda_d}{a}\right)\right)} \quad (35)$$

and the expression for the electric field phasor in tissue on the axis of the patch is:

$$\tilde{E}_t(z) = \frac{\tilde{V}}{\left(\left(\frac{\pi}{2} - \cot^{-1}\left(\frac{\lambda_d}{a}\right)\right)k(f) + \cot^{-1}\left(\frac{\lambda_d}{a}\right)\right)} \frac{1}{a\left(1 + \left(\frac{z}{a}\right)^2\right)} \quad (36)$$

The expression (36) reveals that the electric field in tissue is nearly constant at axial distances from the electrode that are a fraction of the electrode radius. For example, at a distance z=0.33a, the quantity $$\frac{1}{a\left(1 + \left(\frac{z}{a}\right)^2\right)} \approx \frac{1}{a(1.1)} \quad (37)$$

and at $z = 0.5a$ $$\frac{1}{a\left(1 + \left(\frac{z}{a}\right)^2\right)} \approx \frac{1}{a(1.25)} \quad (38)$$

Thus, even at the axial distance of about half the electrode radius the electric field within the tissue changes slowly. However, when z>>a $$\tilde{E}_t(z) \approx \frac{a}{z^2} \frac{\tilde{V}}{\left(\left(\frac{\pi}{2} - \cot^{-1}\left(\frac{\lambda_d}{a}\right)\right)k(f) + \cot^{-1}\left(\frac{\lambda_d}{a}\right)\right)} \quad (39)$$

which shows that the electric field decays rapidly inversely proportional to the square of the axial distance. At the axial distance equal to about 3 times the electrode disc radius, the field decays to about 10% of its value found in close proximity from the disc. This suggests that the patch electrode or any other insulated surface electrode provides nearly uniform field at distances under about half the electrode diameter in tissue when tissue in that region is on the order few electrode diameters thick.

To discuss field magnitudes that could be obtained using patches it is again worth considering different modes of field application. For all modes, the case of thin dielectric $$\frac{\lambda_d}{a} \ll 1$$

is particularly useful. In this case, when $$\frac{z}{a} \leq 0.5,$$

one finds $$\cot^{-1}\left(\frac{\lambda_d}{a}\right) \approx \left(\frac{\pi}{2} - \frac{\lambda_d}{a}\right) \text{ and } \left(\frac{\lambda_d}{a}\right)^2 \ll 1 \quad (40)$$

reducing (39) to $$\tilde{E}_t(z) \approx \frac{\tilde{V}}{a\left(\frac{\pi}{2} + k(f)\frac{\lambda_d}{a}\right)} \quad (41)$$

Consider now the mode of operation where nanosecond (on the order of 10 nanoseconds) are employed. In this mode, using the tissue model in (3), $$k(f) = \frac{(\epsilon_0 j 2\pi f k_t(f) + \sigma_t)}{\epsilon_0 j 2\pi f k_d} = \quad (42)$$

$$\frac{\left(j2\pi \frac{f}{f_t} \frac{1 + j2\pi \frac{f}{f_\beta}}{1 + j2\pi \frac{f}{f_\alpha}} + 1\right)}{j2\pi \frac{f}{f_d}} \approx \frac{f_d}{f_t} \frac{f_\alpha}{f_\beta} = \frac{1}{g} \approx 2 \times 10^2$$

where parameters $f_t$ and $f_d$ were specified in equation (7), while $f_\alpha$ and $f_\beta$ are the lower and higher dispersion frequencies in the tissue model and quantity g is specified in equation (16) for the skin model. Considering specific parameters as an example where a=0.5 cm, $\lambda_d$=500 μm=5×10$^{-2}$ cm, one finds $$\tilde{E}_t(z) \approx \frac{\tilde{V}}{a\left(\frac{\pi}{2} + 20\right)} \approx \frac{\tilde{V}}{20a} = \frac{\tilde{V}}{10}\left(\frac{V}{cm}\right) \quad (43)$$

For the peak voltage of 10 kV, this gives the field magnitude of about 1 kV/cm up to the depth of about 0.25 cm under the patch within tissue.

This electrode can be applied to the exterior or interior of the body. It can be positioned and held in place by a variety of positioning and holding means. The positioning means include by hand, catheter and/or guidewire positioning and deployment, or endoscope or bronchoscope or other similar positioning and deployment means. The holding means include by hand pressure, adhesives, elastic or Velcro straps, or other mechanical attachment means. The electrode is made of rigid, flexible or conformal materials (such as a thin flexible sheet or mask filled with conductive gel) in order to provide intimate contact with the target treatment area of the body. Optionally, a gel such as a hydrogel can be applied between the electrode and the target area in order to ensure adequate distribution of the applied electric field and minimize the potential generation of surface plasma that could lead to heat generation.

Additional configurations of "patch-like" electrodes and other configurations are described below. Using the electrodes described below to apply the electric fields described hereinabove to tissue, it is possible to kill the target cells, such as tumors, carcinomas, lesions, cysts or other undesirable growths, via apoptosis or necrosis while preserving the integrity of the surrounding or underlying tissue. Additionally, it is possible to perform cosmetic treatments by applying the electric field to skin in order to disrupt melanogenesis, for example. Through local killing of tissue having excess pigmentation or disruption of melanogensis, whereupon healing, the skin returns to its normal pigmentation, it is possible to treat such conditions of hyperpigmentation as solar lentigines (brown "liver" spots), freckles, stains, melasmas, pigmented nevi (birthmarks or beauty marks), under-eye dark spots, post-inflammatory hyperpigmentation, and acanthosis nigricans, among others. A specific goal of the electrode design and treatment parameters is to minimize the generation of heat that could diffuse into the surrounding tissue and cause damage beyond the desired area of treatment. Preservation of surrounding tissue is especially desirable in delicate areas of the body, such as blood vessels, cardiac chambers and arteries, esophagus, colorectal passages, stomach, urethra, gynecological passages and tissue, nasal passages, and bronchial tubes.

All of the electrode geometries described herein have a separation layer (e.g., insulating layer) that drastically limits the amount of conduction current that is responsible for undesirable electrochemical reactions, production of reactive species, electrolysis and heating that can lead to tissue necrosis. Such an electrode design enables the generation of electric fields with much higher intensities that can kill targeted cells more rapidly and over larger areas while sparing delicate vessel and/or cavity walls.

Various needle-based electrodes or multiple-needle arrays have also been proposed in the prior art. These configurations are designed to be inserted into the target tissue for treatment (such as a tumor). Such needle-based technologies are not well-suited for killing target cells near delicate, thin-walled internal vessels or body cavities because of the high risk of perforation of these structures. Treatment times can be slow for cases of multiple or large target areas because the needle-based systems must be carefully repositioned and re-inserted into each target. Finally, such electrodes can create highly non-uniform and concentrated electric fields, causing non-uniform treatment at a minimum or local 'sparking' and damage at worst.

The following criteria are useful for selection of the optimal electrode geometry:
1. Well-defined and repeatable distance between the electrode and the target treatment area.
2. Able to accommodate varying sizes, curvatures, and topographies of the target treatment area, such as vessel or chamber curvature, diameter, and length.
3. Maximize area of treatment while meeting the goals of (1) and (2).
4. Ease of manufacturing/assembly
5. Minimize the voltage required to generate sufficient electric field and/or plasma for treatment purposes. Lower operating voltages can lead to reduced costs and size of the power supply and associated electronics.
6. Minimize the generation of electric field non-uniformities that could lead to generation of plasma sparks (high temperature plasma "streamers" like lightning bolts) that concentrate the electrical energy into a highly localized area or areas.
7. Enable scanning of the electrode if cannot treat entire target area while stationary.

One embodiment of an electrode that meets these requirements is an insulated conductor needle, rod or wire having a sharp or rounded end effector with a slightly thinner dielectric coating than along the length of the needle/rod/wire. In the case of an insulated needle, the needle is inserted into the center of the tumor or other target tissue for treatment. Prior to activation, the settings on the generator are adjusted such that the size of the electric field delivered matches the size of the target tissue. In the case of a rod, it is threaded into the desired internal body structure (cavity or vessel) and the rounded end effector is placed in contact with the cavity or vessel wall.

Upon activation of the high voltage waveform generator, the electric field will concentrate into a circular region around the contact area. Steering and deflection mechanisms as well as the electrode configurations such as those shown in U.S. Pat. Nos. 8,583,260, 7,850,685, 8,394,091, 8,419,681, 6,585,718, 5,480,382 and 5,318,525 can be used in such a delivery catheter. Further embodiments of interest are disclosed in U.S. patent application Ser. No. 10/426,923 filed Apr. 29, 2003 and in U.S. patent application Ser. No. 10/754,445, filed Jan. 9, 2004. All patents and publications referenced herein are incorporated by reference herein in their entireties for any purpose whatsoever. These mechanisms allow the treatment electrode to be threaded into the body towards the target area and then brought into contact with it. In contrast to the bare electrodes that are connected to a radiofrequency generator in the aforementioned patents, the electrodes in this embodiment are insulated and connected to a high-voltage waveform generator as described hereinabove. Note also that the wiring within said delivery device must have sufficient insulation to prevent electrical breakdown along the delivery device. The amount of insulation required depends on the applied voltage. Such a system still depends on the operator to ensure that the end effector maintains contact with the body vessel or cavity during treatment.

Alternatively, the catheter may be pre-shaped to conform to the target physiology such that the treatment electrode is automatically placed in intimate contact with the target area upon threading the catheter to the treatment site, such as the wall of the heart as shown in U.S. Pat. Nos. 8,535,303 and 8,486,062. The aforementioned patents are incorporate herein for any purpose whatsoever.

Figure 5:
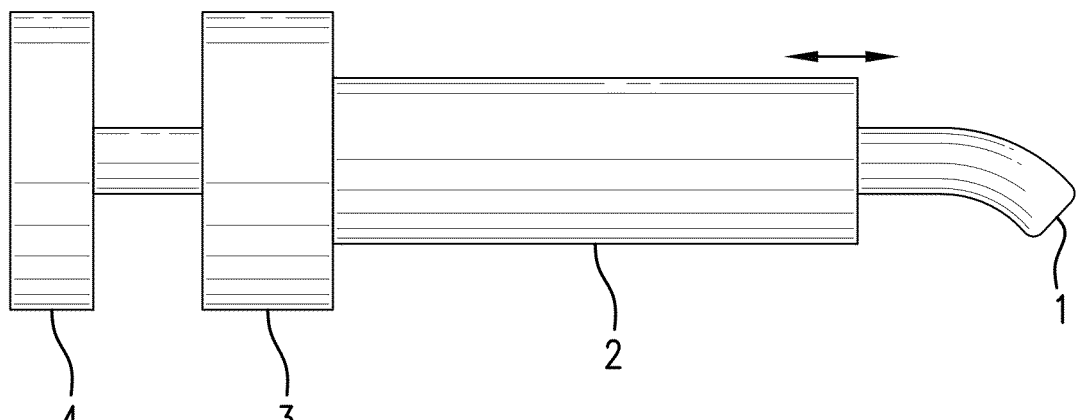
FIG. 5 is a schematic of an exemplary device made in accordance with the disclosure.

In another embodiment as shown in FIG. 5, the aforementioned conductive rod has a plurality of insulated electrical structures (wires or wire tracings) that run axially along an end effector (rounded or flat at the end). Specifically, FIG. 5 shows a catheter having a steerable electrode tip, 1. Upon advancement of the catheter, 2, to the desired location, the tip, 1, is extended by holding the catheter hub, 3, and moving the stylet hub, 4, distally such that the tip, 1, extends. The tip can then be rotated to the target area as desired. The stylet is connected to a waveform generator as described herein (not shown).

Alternating pairs of the wire tracings are electrically connected to high voltage and ground from the pulse generator. As before, the rod is threaded into the desired internal body structure (cavity or vessel) and the end effector is placed in contact with the target area. Steering and deflection mechanisms as well as the electrode configurations such as those shown in U.S. Pat. Nos. 8,583,260, 7,850,685, 8,394,091, 8,419,681, 6,585,718, 5,480,382 and 5,318,525 can be used in such a delivery catheter. These mechanisms allow the treatment electrode to be threaded into the body towards the target area and then brought into contact with it. The aforementioned patents are incorporated herein for any purpose whatsoever. In contrast to the bare electrodes that are connected to a radiofrequency generator in the aforementioned patents, the electrodes in this embodiment are insulated and connected to a high-voltage waveform generator as described hereinabove. Note also that the wiring within said delivery device must have sufficient insulation to prevent electrical breakdown along the delivery device. The amount of insulation required depends on the applied voltage. Alternatively, the catheter may be pre-shaped to conform to the target physiology such that the treatment electrode is automatically placed in intimate contact with the target area upon threading the catheter to the treatment site. The activation of the pulse generator will enable delivery of the electric field to the portion of the target area that is in contact with the wire tracings.

In another embodiment, a helical electrode is screwed into the target tissue site (such as a vessel or cavity) for treatment. The helical electrode such as that shown in FIGS. 1-6 of U.S. Pat. No. 5,431,649 and the accompanying description, is configured to provide a greater surface area for treatment, and is preferably coated with a separation material and connected to a high voltage waveform generator as described above. The aforementioned patent is incorporated herein for any purpose whatsoever.

Figure 6:
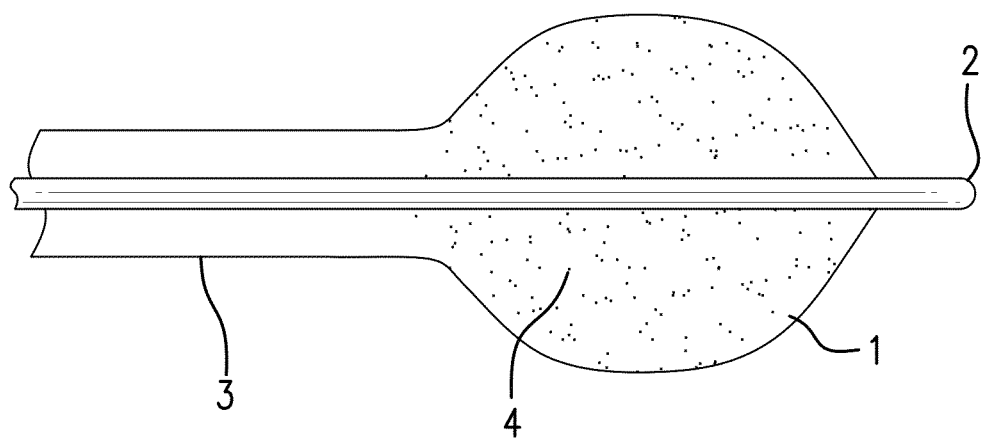
FIG. 6 is a schematic of a further exemplary device made in accordance with the disclosure.

In another embodiment as shown in FIG. 6 herein, a balloon made from a separation material is positioned proximally to the target area by hand or via a feeding catheter and/or guidewire. This balloon is then inflated with a conductive material that is connected electrically to a pulse generator. Upon activation of the high voltage waveform generator, the electric field will then be delivered to the portion of the target area that is in contact with the balloon sides or nearly so. The conductive material could be electrical plasma, liquid, particles, or a composite thereof.

As illustrated in FIG. 6, the balloon, 1, is introduced to the desired location by the guidewire, 2. The catheter, 3, provides a conduit for the introduction of conductive fluid, 4, into the balloon, prior to activation of the waveform generator (not shown). This balloon-based treatment can be especially useful as a replacement for post-surgical therapy after resections of tumors. After the removal of the tumor, radiation or chemotherapy is often employed to make sure that any residual tumor in that area will be killed. By placement of an inflated balloon with a conductive material near its surface, and electric field treatment, such radiation or chemotherapy with their attendant risks and side effects can potentially be avoided. If desired, the balloon can be implanted post-resection, filled, and activated wirelessly as required.

In order to provide intimate contact between the electrode and an irregularly-shaped topography of the tissue surface, such as a surface that may be found after the resection surgery described above, it is useful to provide a separation material between the electrode and the tissue that can conform to this topography. Examples of such a separation material can include liquids, gels, and gases that act as a dielectric insulator or electrically resistive material. These can include but are not limited to oils, conductive fluids, fluids containing conductive materials or particles, gels, and plasmas. These materials can also be used in combination with a solid separation layer.

Figure 7:
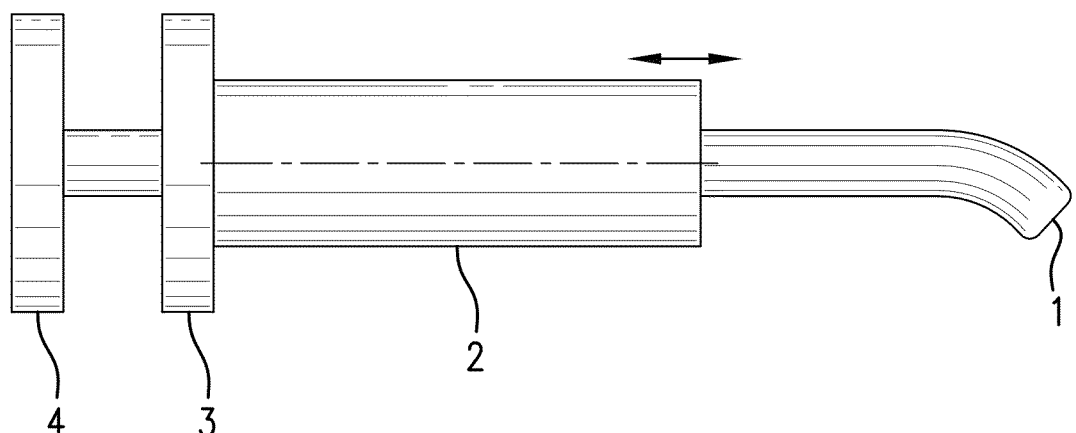
FIG. 7 is a schematic of a further exemplary device made in accordance with the disclosure.

In another embodiment as shown in FIG. 7 herein, the balloon is coated with a conductive layer and then a separation layer. This balloon is connected to the pulse generator, inflated, and activated as before. Note also that the wiring within said delivery device must have sufficient insulation to prevent electrical breakdown along the delivery device. The amount of insulation required depends on the applied voltage.

Figure 8:
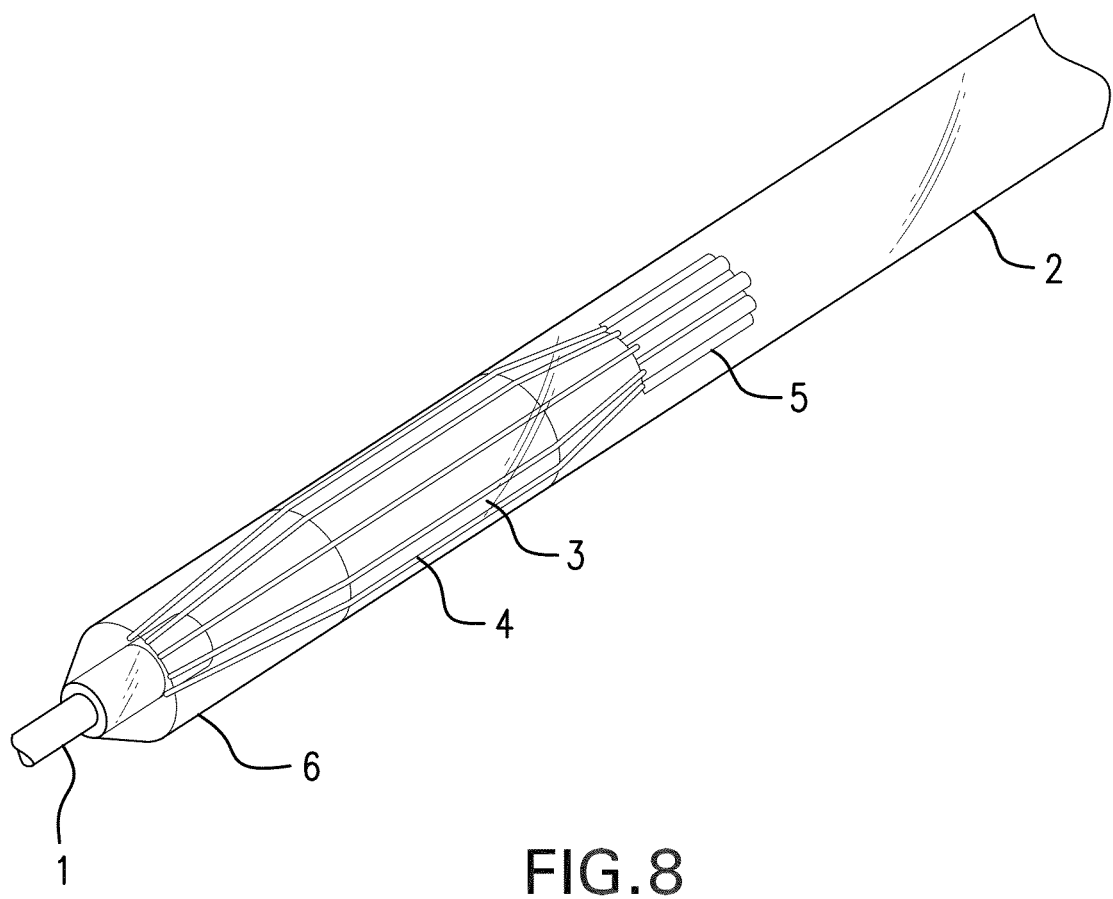
FIG. 8 is a schematic of a further exemplary device made in accordance with the disclosure.

In another embodiment, a balloon having insulated electrical structures that are separate from one another is positioned proximate a target area via a feeding catheter and/or guidewire as shown in FIG. 8, FIGS. 1A and 1B in US Patent application 2013/0184702, and FIG. 11 in U.S. Pat. No. 7,850,685. The aforementioned patents and applications are incorporated herein for any purpose whatsoever. One version of a balloon with insulated electrical structures contains a plurality of insulated wires that run along the outside of the balloon at a defined separation. The depth of the penetration of the electric field can be set based on the separation of the wiring. Other structural configurations are also possible to design for those skilled in the art. The wires are connected to the high voltage waveform generator such that alternating wires are connected to the high voltage output and ground. This balloon is then inflated with a gas such that the insulated electrical contacts are in contact with the target and connected electrically to a pulse generator. As in the previous embodiment, upon activation of the pulse generator the electric field will be delivered to the target area.

Specifically, FIG. 8 shows a balloon-tipped treatment catheter. The guidewire, 1, provides internal support as the catheter, 2, is threaded into position. The balloon, 3, has insulated wiring, 4, which surround the balloon and are joined at the connector, 5, to a wire(s) that connect back to the generator (not shown). The catheter retracts from its initial position, 6, in order to deploy the balloon.

Alternatively, a round or semi-round wire, a plurality of wires, an insulated conductive sheet, or an insulated sheet having a pattern of wire tracings can each be bent into coiled shapes and then threaded into the body to the target area via a delivery catheter. Upon reaching the target area, the coiled wire is deployed from the delivery catheter, as shown in FIGS. 12 and 14 in U.S. Pat. No. 7,850,685. Such wire is made to match the diameter of the target vessel or cavity or slightly larger such that the coil is compressed and preloaded against the target area. Upon activation of the pulse generator, the electric field will be delivered via the coiled wire to the target area.

Similarly, one or more pairs of coiled wires can be provided and threaded into the body to the target area, one wire or set of wires connected to the high voltage output and the other(s) connected to ground as shown in FIG. 6 in U.S. Pat. No. 7,850,685. In all cases, the electrodes described in U.S. Pat. No. 7,850,685 are modified such that they were coated with the desired separation layer as described hereinabove and connected to the appropriate high voltage waveform generator. Note also that the wiring within said delivery device must have sufficient insulation to prevent electrical breakdown along the delivery device (not at the target area). The amount of insulation required depends on the applied voltage.

The above-described electrode configurations can also be delivered to the body via endoscopic, arthroscopic, or laparoscopic means, as shown for example, in FIGS. 1-6 of US Patent Publication no. 2013/0261389. The aforementioned patent application is incorporated herein for any purpose whatsoever. Note that the electrodes in the above mentioned application would be modified to include a separation layer. Optionally, one or more of these wires could be employed (both monopolar and bipolar operation is possible) and connected to the desired high voltage waveform generator.

All delivery devices also can provide additional capabilities that can aid in the identification, targeting, and diagnosis of the target treatment area, such as in imaging and electrical detection. Such delivery devices can provide capability for application of liquids, creams, and/or gels that serve as a separation layer and aid in the creation of a conformal contact to a curved or otherwise irregular target tissue topography. Such application means include, injectors, needles, hoses, ports, and the like, which may be driven via syringes, pumps, pressurized gas cartridges, or other fluid motion-inducing systems.

Control of the treatment procedure is accomplished through a variety of methods as described in U.S. patent application Ser. No. 13/943,012, filed Jul. 16, 2013 originally filed as International Application No. PCT/US2012/031923, filed Apr. 2, 2012 and International Application No. PCT/US2012/055726, filed Sep. 17, 2012. Each of the aforementioned applications is incorporated by reference herein in its entirety for any purpose whatsoever.

Figure 9A:
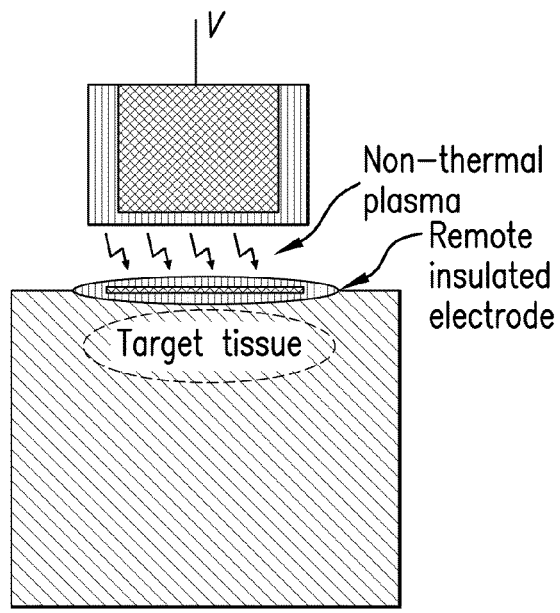
FIGS. 9A-C illustrate further embodiments in accordance with the disclosure.
Figure 9B:
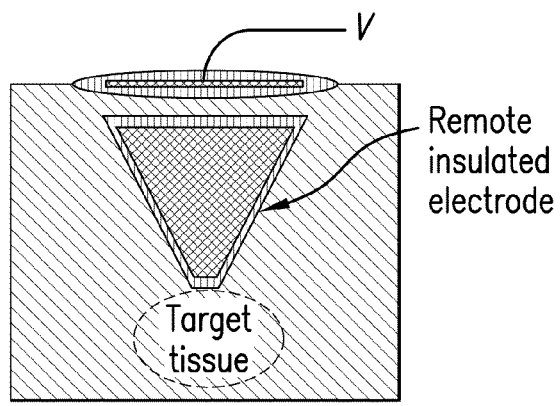
Figure 9C:
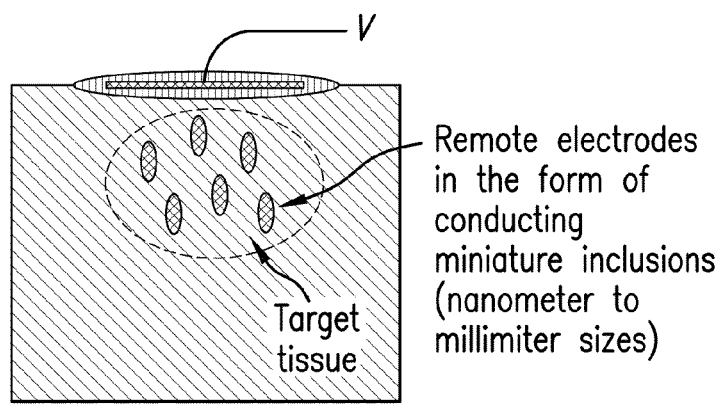

Creating pulses of relatively strong electric field without the need to also transfer currents from the electrodes into tissues also makes it possible to employ remote conducting electrodes that are not connected by current carrying conductors to the source of voltage or current pulses in order to generate sufficiently strong pulses of electric field in target tissues. A few examples of the use of remote electrodes are shown in FIG. 9. FIGS. 9A-C illustrates that the remote electrodes can be shaped and positioned on or within tissue to focus or intensify the electric field around the targeted tissue region when an external field is applied by connecting a generator of pulsed voltage to another control electrode. In some cases, as illustrated in FIG. 9, the remote electrode can be connected to the control electrode with a brief occurrence of plasma that transfers charge to the remote electrode. The remote electrode may be used without insulation in some cases as it has no direct electrical connection to the external generator capable of supplying the conduction current.

Figure 10A:
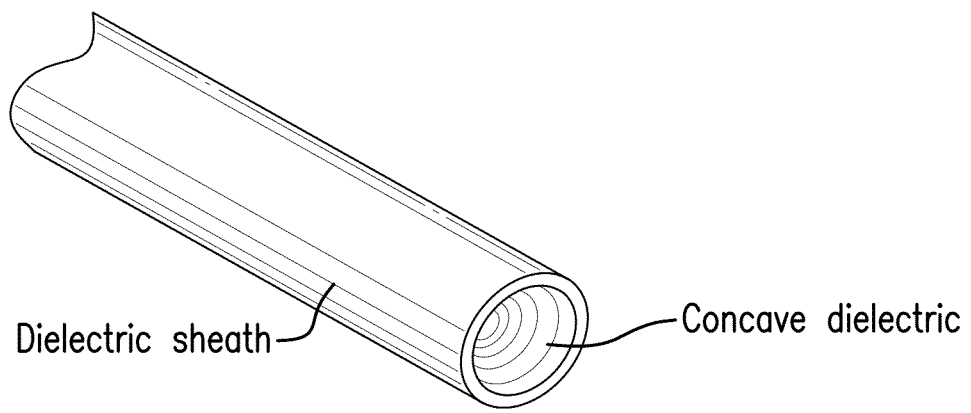
Figure 10B:
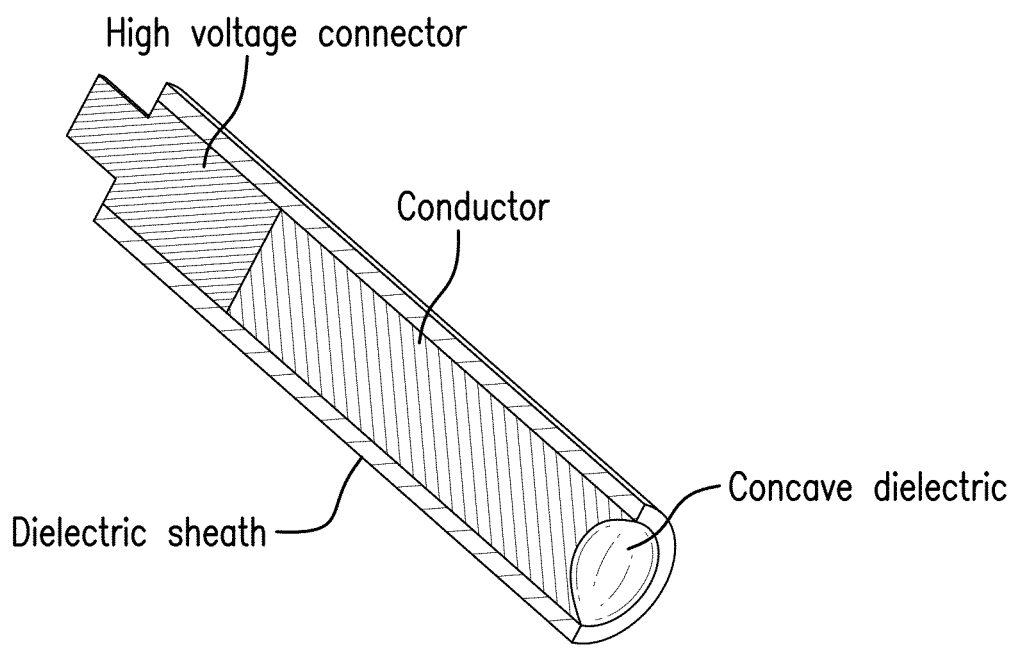
Figure 10C:
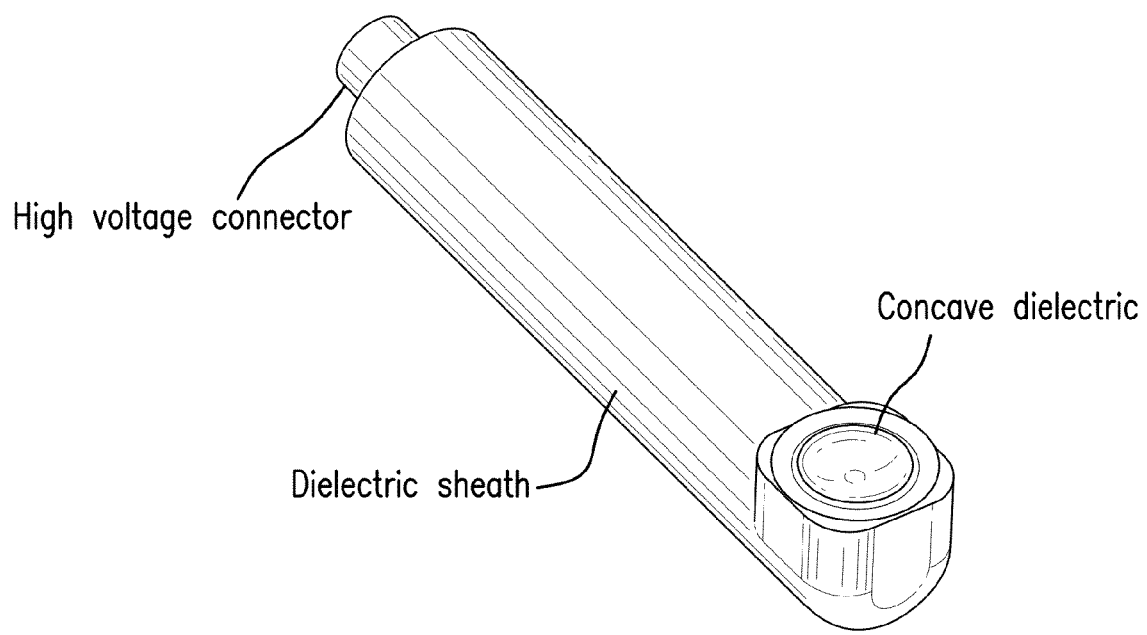

FIGS. 10A-10C illustrate further embodiments of an electrode probe in accordance with the disclosure, wherein FIG. 10A illustrates an elongate insulated electrode with a concave treatment tip, FIG. 10B illustrates a cross section of the embodiment of FIG. 10A, and further wherein FIG. 10C illustrates a variation of the electrode of FIG. 10A wherein the concave treatment tip is on a side of the probe. As illustrated, each probe has a proximal end attached to a high voltage connector, a distal end having a treatment tip, and an outer peripheral generally cylindrical surface that is covered with a layer of electrically insulating material in the form of a dielectric sheath. A concave treatment tip is provided at the distal end of the probe of FIG. 10A having a dielectric coating that may be thinner (or otherwise less resistive) than the dielectric sheath that coats the probe. If desired, this concave probe can be positioned on the side of the probe as illustrated in FIG. 10C. If desired, the probe can be used to generate a local plasma discharge within the concavity and also apply an electrical field to the tissue or alternatively may be configured to not substantially create a plasma and merely apply an electrical field to the tissue. The concave portion of the electrode can be patterned to have regions of varying electrical resistance across the dielectric, such as by varying the thickness of the dielectric to form a grid pattern bumps, or the like.

FIGS. 11A-11J illustrate various examples of implementations of insulator/electrode arrangements for delivery of electric field pulses into tissues. The lighter color in the figures corresponds to insulating material such as silicone, PEEK, PVDF and others. The black color in the figures corresponds to solid conducting materials such as copper and the like. Where indicated, fluid or gel material ("G") can be provided that can act as conducting material capable of flowing or otherwise changing its shape in three dimensions.

Figure 11A:
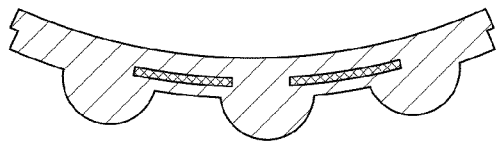
FIGS. 11A-11J illustrate further embodiments of electrode heads.

FIG. 11A illustrates an insulated multi-conductor electrode. Breakdown of air in the form of electron avalanches and ionization may electrically short the gap between the insulated surface of the electrode and the surface of tissue as illustrated in FIGS. 11F-11G. This air breakdown will usually occur during sub-intervals of time shorter than the voltage pulse. The filling of the gap between the insulated electrode surface and tissue by ionized gas may depend on the rise and fall time of the voltage. In some cases, usually when the rise times are longer than few nanoseconds, the ionized gas will tend to occur with greater likelihood near the bumps. The different conductors can be electrically connected to the same or different potentials. When they are connected to the same potential source, the electric field is mostly perpendicular to the electrode surface over the entire electrode surface, as illustrated in FIG. 11F. When the electrodes are connected to different potential sources (such as high and ground, respectively), the electric field is mostly perpendicular to the electrode surface where the conductor is extended and mostly parallel to the electrode surface between the conductor areas, as illustrated in FIG. 11G.

Figure 11B:
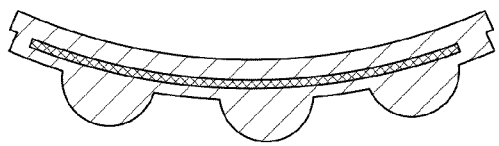

FIG. 11B illustrates an insulated electrode with a contiguous conductor indicated by the dark arcuate line. When a high voltage pulse is connected to that conductor, an electric field is created mainly perpendicularly to the electrode surface over nearly the entire electrode surface.

The pattern of ionized gas formation under the electrode may also depend on the relative position of the conductors with respect to bumps or protrusions on the insulator surface. For example, as shown in FIG. 11H, the plasma breakdown region may be confined to be near the surface of the bumps or protrusions when the conductor is place over these bumps or protrusions. FIG. 11D illustrates that not every conductor may be insulated in order to avoid conduction current through tissue. FIG. 11I illustrates how this type of electrode may be employed in delivering pulses of electric field into tissues.

Figure 11C:
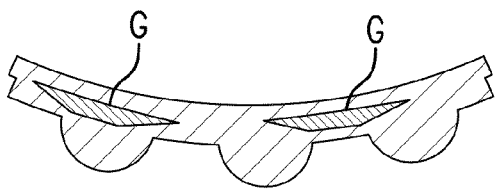
Figure 11E:
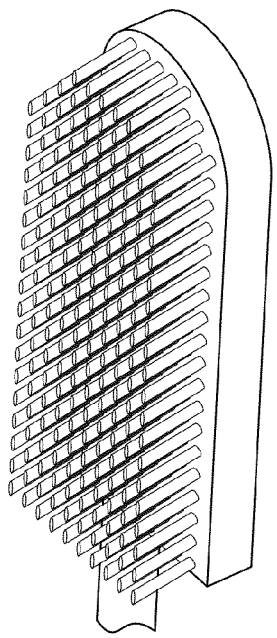
Figure 11D:
Figure 11F:
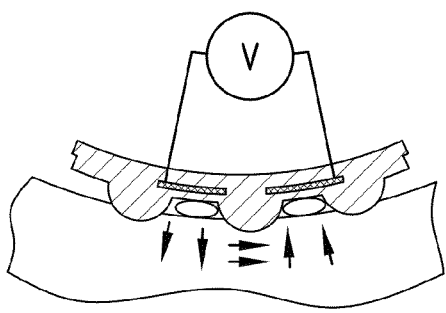
Figure 11G:
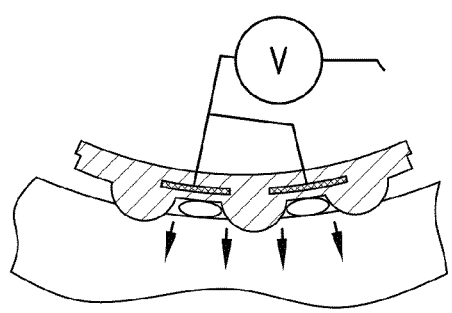
Figure 11H:
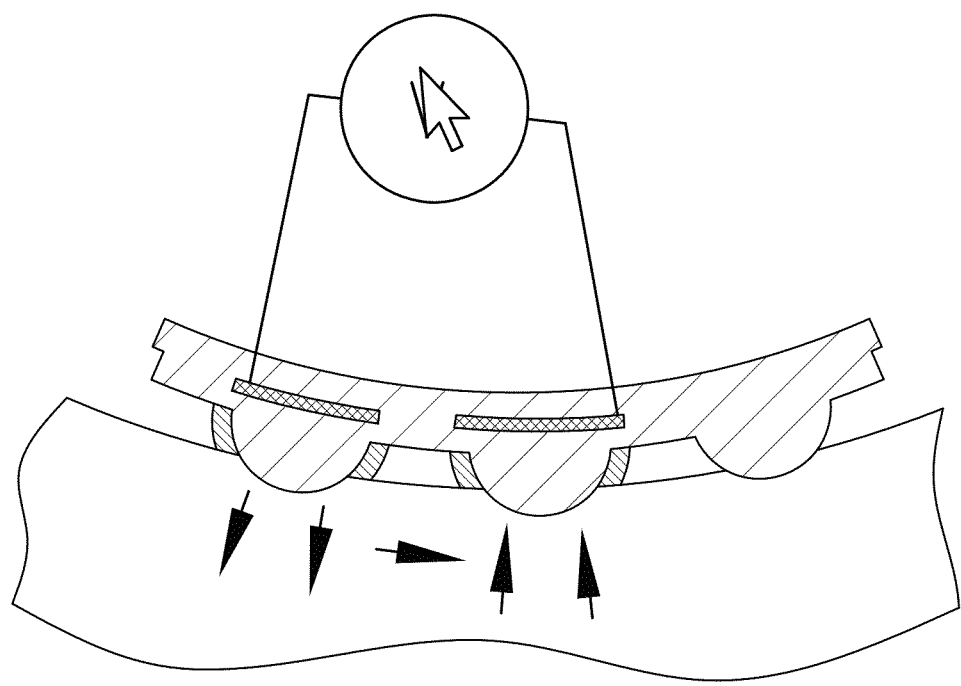
Figure 11I:
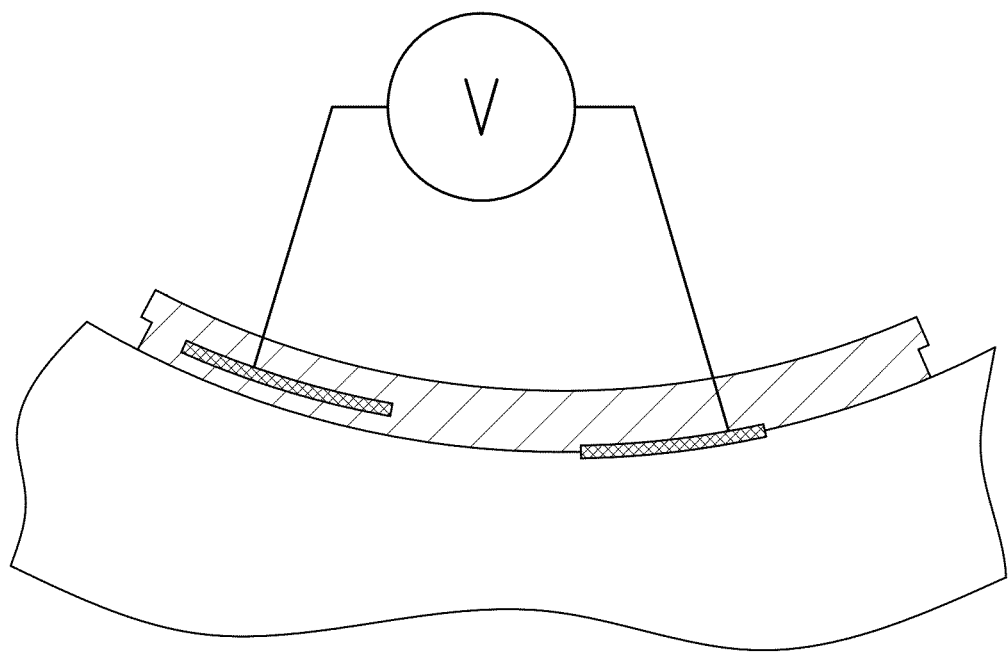
Figure 11J:
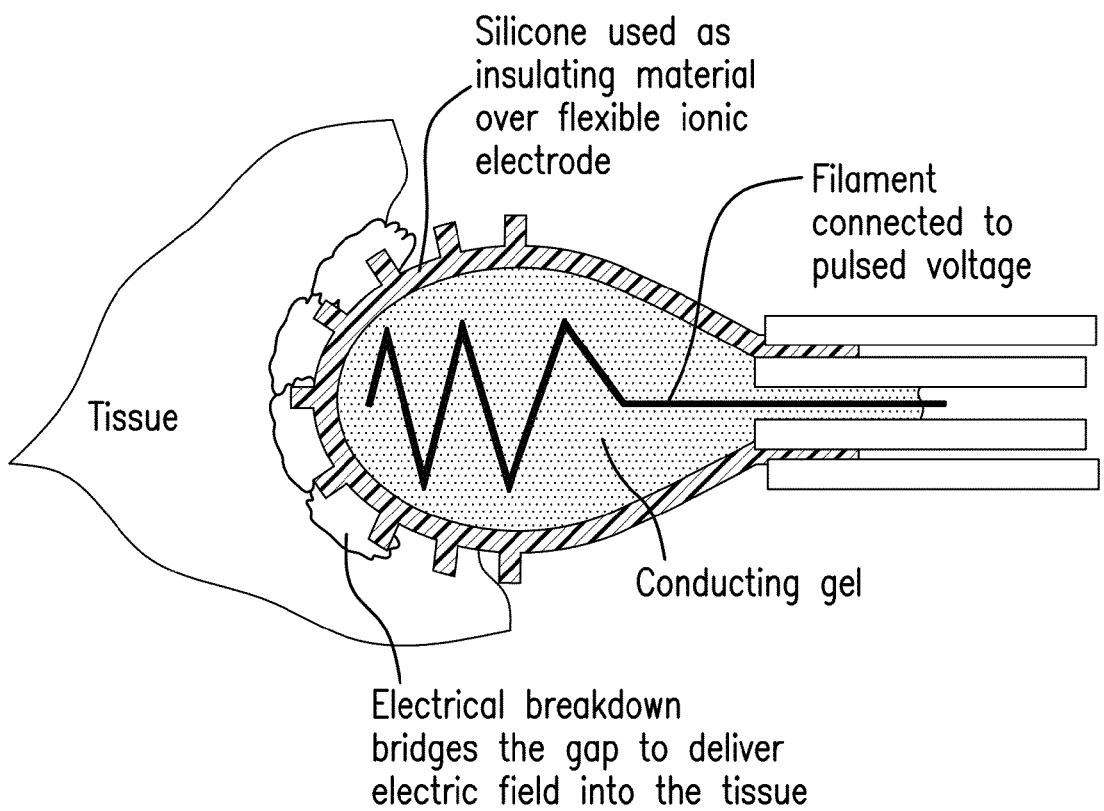

FIG. 11C shows that conducting material surrounded by the insulator need not necessarily be a solid conductor. Although solid conducting materials such as aluminum or copper metal have high conductivity, they may suffer from undesirable mechanical failures (cracks for example) when the electrode is stretched. When this is an issue, it may be convenient to replace solid conductors with conducting gels, fluids or clays. One advantage of using fluid is the possibility of filling different channels within the insulator thereby providing the possibility of having a reconfigurable structure of conducting material within the insulated electrodes. The possibility of using relatively low conductivity materials to form conducting structures within insulated electrodes arise due to the fact that the applications being discussed herein require high electrical field strength during pulse durations, but relatively low power. Having no current or very low current in some cases through the electrode conductors circumvents concerns typical in RF ablation applications related to electrode heating and conductor voltage drop. One example where the use of conducting gel electrode helps make the electrode conformal to the tissue is shown in FIG. 11J. Note that the electric field distribution in the relatively low-conductivity materials may vary more significantly as the amount of material in the stretchable electrode increases. In such cases, a metallic or otherwise highly conductive material in the form of a wire or coil or other shape may be inserted into the low-conductivity material (gel, fluid, etc) to minimize the variation of the electric field within the overall stretchable electrode.

FIG. 12A is a perspective view of an embodiment of a magnetically assisted steering catheter system configured to deliver a time varying electrical field to tissue to be treated located at an anatomical target region. FIG. 12B is a cross-sectional detail of a distal end of the system of FIG. 12A, showing a guidewire inserted through the system, and FIG. 12C is a cross-section of the system of FIG. 12B, taken along line 3-3. Referring to FIG. 12A, a magnetically assisted steering catheter system 10 is shown. The system 10 generally includes a catheter 20 configured to be introduced through the vasculature of the patient, and into a three-dimensional anatomical cavity, such as the heart, or through a natural or surgeon created opening such as into the gastrointestinal tract, thoracic cavity, abdominal cavity, and the like, where it can be used to apply an electrical field to the tissue and map the tissue, if desired. As illustrated, the system can further include an electrophysiology mapping processor 14 used to electrophysiologically map tissue with the catheter 20. The system further includes a source of electrical energy as described herein, for delivering a time varying voltage waveform to the catheter 20 in order to impose an electrical field over a desired target location. A guidewire 30 is also provided for facilitating introduction of the catheter 20 through the tortuous vasculature of the patient.

Referring further to FIGS. 12B and 12C, the guidewire 30 is configured to be slidably disposed within the catheter 20. The guidewire 30 includes an elongate flexible body 31 having a proximal end 32 and a distal end 34. The guidewire body 31 is composed of a flexible and resilient material, for example, a superelastic alloy such as Nitinol, or alternatively is composed of a material such as titanium, tantalum, or stainless steel. The outer diameter of the guidewire body 31 is approximately 0.020 inches (0.51 mm). The length of the guidewire body 31 is sufficient to pass through the entire length of the catheter 20. In an exemplary embodiment, the length of the guidewire body 31 is approximately 180 to 220 cm.

If desired, the guidewire 30 can further comprise a magnetically attractive element 36 disposed on the distal end 34 of the guidewire 30. The magnetically attractive element 36 may be secured to the distal end 34 by welding, brazing, gluing, other suitable adhesive, and the like. The magnetically attractive element 36 can take the form of an element that moves in response to a magnetic field. For example, the magnetically attractive element 36 can include a permanent magnetic material, such as neodymium-iron-boron, or can comprise a ferrous material, such as cold rolled steel or iron-cobalt alloy. The magnetically attractive element 36 can also take the form of an electromagnet connected to wires (not shown) that are passed in conventional fashion through a lumen (not shown) extending through the guidewire 30.

The catheter 20 generally includes an elongate flexible catheter body 21 having a proximal end 22 and a distal end 24, and a guidewire lumen 35 extending through the length of the catheter body 21. The guidewire lumen 35 is sized to receive the guidewire 30. In the illustrated embodiment, the catheter body 21 comprises a unibody design; that is, it is formed from a single extrusion in accordance with methods used by a person of ordinary skill in the art. Alternatively, a two piece catheter body (not shown), such as a proximate member (not shown) and a distal member (not shown) may be bonded together at an interface (not shown) with an overlapping thermal bond or adhesively bonded together end to end over a sleeve in what is referred to as a "butt bond."

In the illustrated embodiment, the catheter body 21 is about 5 to 9 French in diameter with a length about 80 cm to 115 cm. The catheter body 21 is composed of a biocompatible thermoplastic material, such as Pebax® material (polyether block amide) and stainless steel braid composite, which has good torque transmission properties. In some implementations, an elongate guide coil (not shown) may also be provided within the catheter body 21. The distal end 24 of the catheter body 21 preferably includes a radiopaque compound, such as barium, so that the catheter 20 can be observed using fluoroscopic or ultrasound imaging, or the like. Alternatively, radio-opaque markers (not shown) can be placed along the distal end 24 of the catheter body 21.

The catheter body 21 has a resilient structure that facilitates the functionality of the magnetically assisted steering catheter system 10. To this end, the catheter 20 includes a spring member 29 positioned inside of and passing through the length of the catheter body 21. The shape of the catheter body 21 is achieved through the use of the spring member 29. To improve the torqueability of the catheter body 21, which is important to the predictable and controlled movement of the distal end 24, the spring member 29 in the illustrated embodiment is formed of a unibody structure, and affixed so that a torsional force applied to the proximal end 22 is transmitted to the distal end 24 of the catheter body 21 without significant loss.

The catheter 20 can further include an electromagnet 26 carried by the distal end 24 of the catheter body 21, one or more operative elements, and in particular, an electrode 25 surrounded by an insulating sleeve or layer "I" and, if desired, a mapping element 27 carried by the distal end 24 of the catheter body 21, and a handle assembly 40 mounted to the proximal end 22 of the catheter body 21. The electromagnet 26 may take the form of a coiled solenoid or an induction electromagnet secured to the distal end 24 using suitable means, such as by welding, brazing, gluing, other suitable adhesive, and the like, depending on the materials from which the electromagnet 26 and the catheter body 21 are made. The catheter 20 further includes two leads 23a, 23b extending through the catheter body 21 from the electromagnet 26 towards the proximal end 22 of the catheter body 21 for coupling to a source of electrical energy.

Electrical current is supplied to the electromagnet 26 via lead wire 23a and returned by return wire 23b to induce a first magnetic field. Polarity through the electromagnet 26 is reversed to induce a second magnetic field in an opposite direction from the first magnetic field. The electromagnet 26 is configured for generating a sufficient magnetic field to deflect (shown in phantom in FIGS. 12A-12C) or otherwise manipulate the magnetically attractive element and/or tip 36 on the distal end 34 of the guidewire 30. The electromagnet 26 may be configured to generate higher magnetic fields for heavier guidewires, and/or guidewires that have distal ends 34 further away from the electromagnet 26.

The strength of the magnetic field generated by the electromagnet 26 depends upon a number of factors, such as the geometry of the electromagnet 26, the material from which the electromagnet 26 is made, and/or the amount of power supplied to the electromagnet 26. In the illustrated embodiment, the power delivered to the electromagnet 26 is fixed at a set level when activated to deliver sufficient power to deflect (shown in phantom in FIGS. 12A-12C) the guidewire tip 36 within a prescribed distance from the electromagnet 26. Alternatively, the power delivered to the electromagnet 26 may be adjustable. In this case, during use, the power is incrementally increased until a desired magnetic field intensity is achieved, and therefore sufficient to deflect the guidewire tip 36 an incremental distance from the electromagnet 26.

In another embodiment, the electromagnet 26 may include a plurality of portions with each portion electrically isolated from the other portion(s). Each of the portions can be electrically connected to the source of energy (not shown), and may be individually or collectively activated to generate a magnetic field. If a weak magnetic field is desired, then only one of the portions is activated. If a relatively stronger magnetic field is desired, then one or more additional portions are activated. Further details on one embodiment of the electromagnet 26 are disclosed in U.S. Pat. No. 6,961,620, which is expressly incorporated herein by reference.

In alternative embodiments, the distal end 24 of the catheter body 21 can carry the magnetically attractive element 36 instead of the electromagnet 26, and the distal end 34 of the guidewire body 31 can carry the electromagnet 26 instead of the magnetically attractive element 36.

In the illustrated embodiment, the insulated electrode 25 takes the form of a linear electrode assembly that includes insulated ring electrodes 25a, 25b mounted on the distal end 24 surrounded by an insulating layer I. Notably, the split nature of the electrode 25 provides selective monopolar and bipolar functionality to the catheter 20. That is, one or both of the insulated ring electrodes 25a, 25b can be configured as one pole of a monopolar arrangement, so that energy emitted by one or both of the electrodes 25a, 25b is returned through an indifferent patch electrode (not shown) externally attached to the skin of the patient; or the ring electrodes 25a, 25b can be configured as two poles of a bipolar arrangement, in which energy emitted by one of the ring electrodes 25a, 25b is returned to the other electrode. The combined length of the electrodes 25a, 25b is preferably about 6 mm to about 10 mm in length. In one embodiment, each electrode 25a, 25b is about 4 mm in length with 0.5 mm to 3.0 mm spacing.

In the illustrated embodiment, the electrodes 25a, 25b can include solid rings of conductive material, like platinum, or can comprise a conductive material, like platinum-iridium or gold, coated upon the device using conventional coating techniques or an ion beam assisted deposition (IBAD) process. For better adherence, an undercoating of nickel or titanium can be applied. Any combination of the electrodes can also be in the form of helical ribbons or formed with a conductive ink compound that is pad printed onto a nonconductive tubular body. A preferred conductive ink compound is a silver-based flexible adhesive conductive ink (polyurethane binder), however other metal-based adhesive conductive inks such as platinum-based, gold-based, copper-base, etc., is also contemplated. Such inks are more flexible than epoxy-based inks. The insulation disposed on the ring electrodes 25a, 25b can be any suitable insulating material, such as silicone, PEEK, PVDF and the like in any suitable thickness to facilitate application of an electric field to the anatomical region of interest, preferably without substantially heating the surrounding tissue via joule heating.

The electrodes 25a, 25b can be electrically coupled to individual wires (not shown) disposed within the catheter 20 where the wires (not shown) are electrically coupled either directly to a connector (not shown) that is received in a port on the handle assembly 40 or indirectly to the connector via a PC board (not shown) in the handle assembly 40. The connector (not shown) plugs into the voltage waveform generator 16 (shown in FIG. 12A).

The handle assembly 40 includes a handle 41, a steering mechanism 42, an electrical connector 52, and a guidewire port 50 associated with the handle 41. The handle 41 is preferably composed of a durable and rigid material, such as medical grade plastic, and is ergonomically molded to allow a physician to more easily manipulate the catheter 20. The steering mechanism 42 includes a steering switch 44 configured to be actuated from a first position (off), which prevents electrical energy from the energy source from energizing the electromagnet, to a second position (on), which allows electrical energy from the energy source (not shown) to energize the electromagnet 26. As a result, the energized electromagnet 26 pulls the magnetically attractive element 36, thereby deflecting the distal end 34 of the guidewire body 31 from a straight geometry to form a simple curve (i.e., a curve that lies in a single plane) (shown in phantom in FIGS. 12A-12C). The steering switch 44 is configured to be actuated back to the off position to allow the resiliency of the guidewire body 31 to flex itself back into a straight geometry.

Although the steering mechanism 42 has been described as unilaterally bending the proximal end 34 of the guidewire body 31 into the curved geometry, the steering mechanism 42 could be modified to bilaterally bend the distal end 34 of the guidewire 30 into two opposite curved geometries along a single plane, e.g. by actuating the steering switch 44 to a third position, that energizes the electromagnet 26 with a reverse polarity. As a result, the energized electromagnet 26 may push the magnetically attractive element 36, thereby deflecting the distal end 34 of the guidewire body 31 opposite the aforementioned simple curve. In this case, the off position may be between the two on positions, such that the switch 44 must pass through the off position when changing the polarity of the electromagnet 26.

In the illustrated embodiment, the guidewire port 50 may comprise a luer lock connector (not shown) through which the guidewire 30 is introduced. Optionally, the guidewire port 50 may have numerous uses in addition to facilitating introduction of the guidewire 30. For example, the guidewire port 50 can provide access for the introduction of other flexible elongate tools or apparatus during a surgical procedure, and can provide a connection to a source of fluid such as saline or contrast (not shown). The conduit 52 facilitates electrical connectivity of the operative elements of the catheter 20 with the processor 14, the waveform generator 16 and the source of energy (not shown) by providing a path for conductors or wires (not shown). The wires (not shown) may couple to the aforementioned connector (not shown) or the PC board (not shown).

FIGS. 13A-D illustrate a further embodiment of a catheter in accordance with the present disclosure with an umbrella tip, wherein a carrier assembly includes multiple carrier arms. Catheter 50, is constructed of biocompatible materials suitable for percutaneous advancement through the vasculature of a patient, and for navigation within the patient's heart. Various tubular body members and shafts are constructed of extruded materials such as Pebax, silicones, polyurethanes, polymers, elastomers, flexible plastics and combinations of these. Catheter 50 includes a distal tip 94, which is made of materials to be atraumatic to tissue. Catheter 50 further includes outer shaft 76 that preferably has a diameter between 8 and 9 Fr and is constructed to provide sufficient stability and torque through the procedure. Catheter 50 includes a carrier assembly 85, which includes multiple electrode elements 92 that are each surrounded by an insulating layer mounted to distal carrier arms 88.

The insulated electrodes 92 and other components of carrier assembly 85 are configured to flex to conform to pulmonary vein ostia and other applicable tissues. Outer shaft 76 can be advanced forward to change the shape of carrier assembly 85 and cause one or more insulated electrodes 92 to contact tissue. Outer shaft 76 slidingly receives inner shaft 78, which is fixedly attached to proximal carrier arms 86. Distal carrier arms 88 are fixedly attached to distal tip 94 and the distal end of control shaft 84. Proximal carrier arms 86 are pivotally attached to distal carrier arms 88, such that advancement and retraction of control shaft 84 relative to inner tube 78 causes the diameter of carrier assembly 85 to contract and expand respectively, such as to cause the carrier assembly to expand to a 4-5 mm diameter. Inner shaft 78 further provides columnar strength to allow an operator to advance inner shaft 78 and cause carrier assembly 85 to properly contact tissue, such as to conform to non-circular pulmonary vein ostia. Inner shaft 78 preferably is attached to a pull wire (not shown), near its distal end, which is operably connected to a control on the proximal end of device 50 allowing an operator to controllably deflect the distal portion of device 50.

The distal end of outer shaft 76 includes a shaft tip 82, configured to radially expand when carrier assembly 85 is retracted. The proximal end of outer shaft 76 preferably includes a handle, not shown, but including one or more controls, such as knobs or levers, such as to advance and retract inner shaft 78 and control shaft 84. The proximal end of device 50 includes one or more connectors for connecting to a waveform generator for delivering an applied voltage to the insulated electrodes 92. In an alternative embodiment, one or more proximal control arms 86 are attached to a second control shaft such that the symmetry of the geometry of carrier assembly 85 can be adjusted to conform to asymmetric pulmonary vein ostia. In another alternative embodiment, device 50 is configured to be inserted over a previously placed guidewire.

Figure 13A:
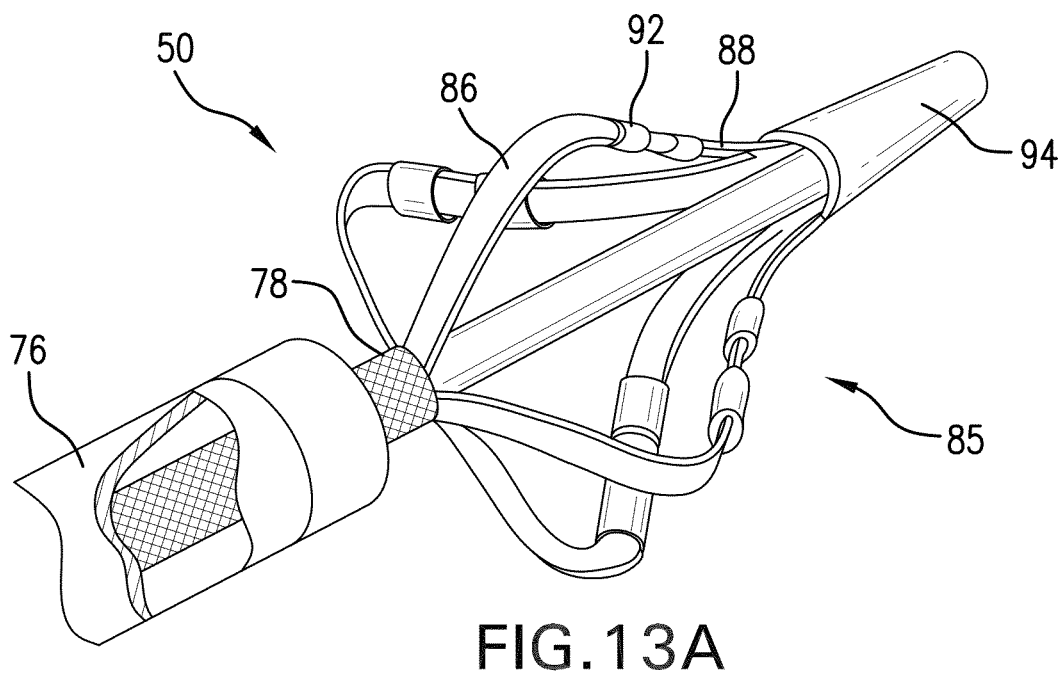
FIGS. 13(A)-13(E) illustrate further embodiments of devices for applying electrical fields to tissue.
Figure 13B:
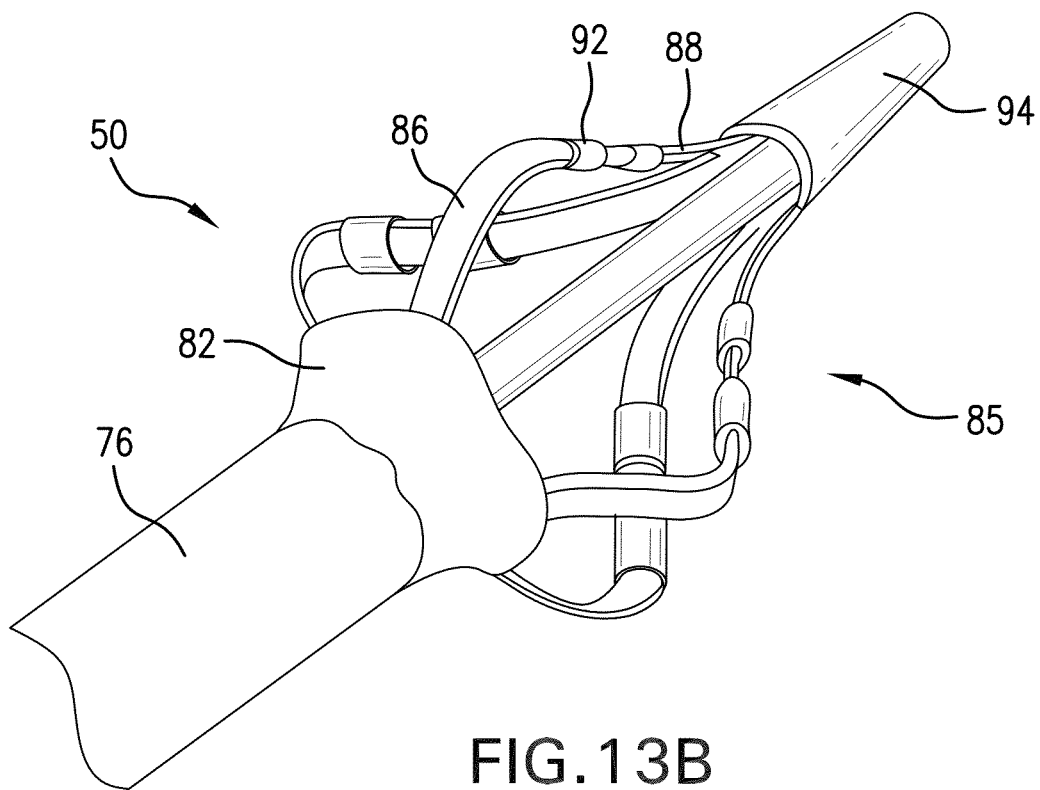

Referring now to FIGS. 13A and 13B, the distal portion of the device 50 is illustrated. FIG. 13A depicts carrier assembly 85 fully expanded, with inner shaft 78 fully advanced. FIG. 13B depicts inner shaft 78 partially retracted such that proximal arms 86 are being captured and radially compressed by shaft tip 82, which expands, as shown, to create a smooth transition of carrier assembly 85 into the inner lumen of outer shaft 76.

Figure 13C:
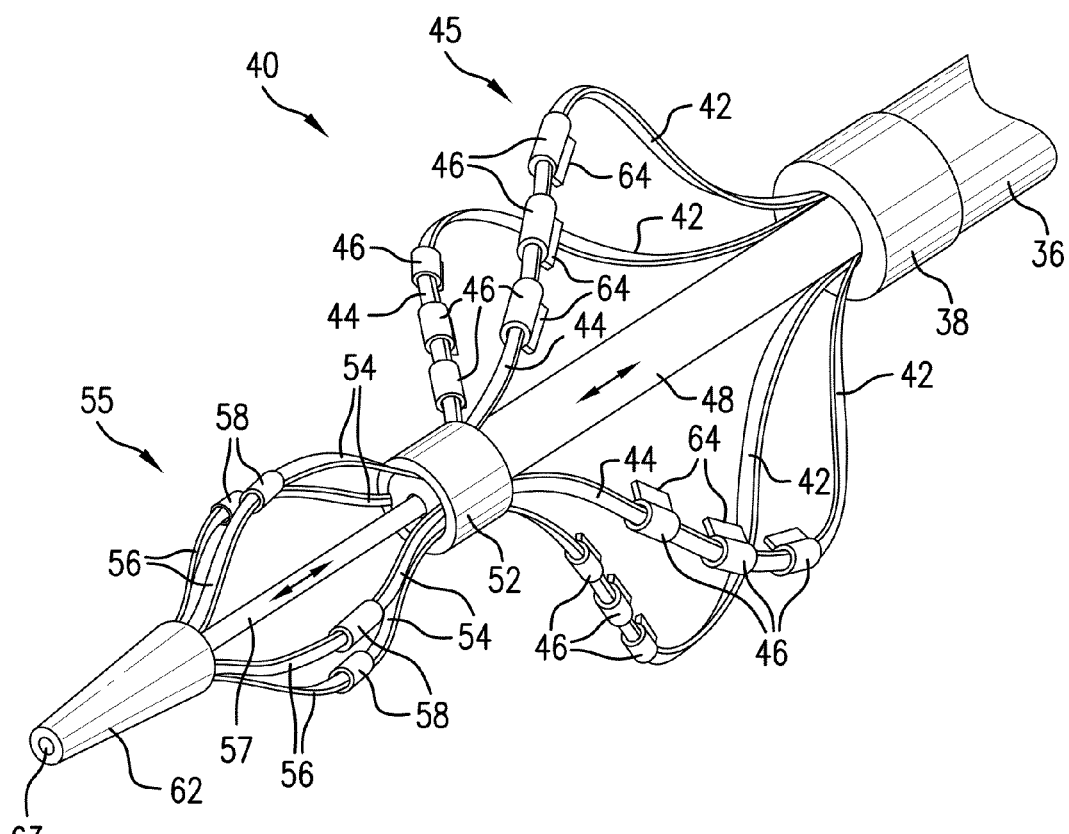

Referring now FIG. 13C, a catheter of the present disclosure is illustrated comprising two carrier assemblies disposed serially along a single axis, with each carrier assembly in an umbrella tip configuration. Catheter 40 includes an elongate tube, outer shaft 36, preferably constructed of Pebax material and approximately 6-8 Fr in diameter, which slidingly receives first control shaft 48. First control shaft 48 is attached on its distal portion to first carrier assembly 45, comprising multiple carrier arms and insulation coated electrodes configured to deliver an time varied electric field via a time varying applied voltage waveform. The proximal end of first control shaft 48, not shown, is attached to a control on the proximal end of catheter 40 configured to allow an operator to precisely advance and retract first control shaft 48. First control shaft 48 includes ring 52 on its distal end that fixedly attaches one end of each distal carrier arm segment 44 to first control shaft 48. Each distal carrier arm segment 44 is pivotally attached on its opposite end to one end of a proximal carrier arm segment 42. The opposite end of each proximal arm segment 42 is fixedly attached to the distal end of outer shaft 36 via ring 38. Distal carrier arm segments 44 and proximal arm segments 42 are constructed of a flexible material, such as Nitinol, and can be resiliently biased in a straight or umbrella tip configuration. Advancement and retraction of first control shaft 48 changes the diameter of carrier assembly 45, including a fully compacted (minimal diameter) radial state when first control shaft 48 is fully advanced, and a maximum diameter state when first control shaft 48 is fully retracted.

Fixedly mounted to distal arm segments 44 are insulated electrodes 46, configured to apply a time varying electric field to tissue. If desired, the electrodes 46 can include fins 64 configured to reside in a flow of blood during E field application. Electrodes 46 are configured to deliver monopolar, bipolar or a combination of monopolar and bipolar energy. Electrodes 46 can include integral temperature sensors if desired, such as a thermocouple welded to an internal portion of the electrode 46. Electrode 46 and any integral temperature or other sensors, are attached to wires, not shown, which travel proximally to the proximal portion of catheter 40 for attachment to an energy delivery unit, a mapping unit, and/or another electronic device for sending or receiving signals and/or power.

First control shaft 48 slidingly receives second control shaft 57. Second control shaft 57 is attached on its distal portion to second carrier assembly 55, comprising multiple carrier arms and electrodes configured to map electrical activity. The proximal end of second control shaft 57, not shown, is attached to a control on the proximal end of catheter 40 configured to allow an operator to precisely advance and retract second control shaft 57. Second control shaft 57 includes tip 62 on its distal end that fixedly attaches one end of each distal carrier arm segment 56 to second control shaft 57. Tip 62 is preferably constructed of a soft or flexible material such as a soft plastic or elastomer chosen to be atraumatic to tissue, and is preferably radiopaque such as a Pebax material doped with Barium Sulfate. Distal tip 62 is constructed to help navigation into and stabilization within a pulmonary vein. Distal tip 62 includes guidewire lumen 63, which is in fluid communication with an internal lumen of second control shaft 57, the lumen traveling to and exiting a proximal portion of catheter 40, such that catheter 40 can be percutaneously inserted into the vasculature of a patient over a guidewire.

Each distal carrier arm segment 56 is pivotally attached on its opposite end to one end of a proximal carrier arm segment 54. The opposite end of each proximal arm segment 54 is fixedly attached to the distal end of first control shaft 48 via ring 52. Distal carrier arm segments 56 and proximal arm segments 54 are constructed of a flexible material, such as Nitinol, and can be resiliently biased in a straight or umbrella tip configuration. Advancement and retraction of second control shaft 57 changes the diameter of carrier assembly 55, including a fully compacted (minimum diameter) radial state when second control shaft 57 is fully advanced, and a maximum diameter state when second control shaft 57 is fully retracted.

Fixedly mounted to distal arm segments 44 are insulated electrodes 58, configured to apply electric field and/or map electrical activity present in tissue. Insulated electrodes 58 can be constructed of a conductive material such as platinum or a combination of platinum and iridium, and coated by a dielectric material. Electrodes 58 preferably include integral temperature sensors, such as a thermocouple welded to an internal portion of the electrode 58. Electrode 58 and any integral temperature or other sensors, are attached to wires, not shown, which travel proximally to the proximal portion of catheter 40 for attachment to a mapping unit, an energy delivery unit, and/or another electronic device for sending or receiving signals and/or power.

Figure 13D:
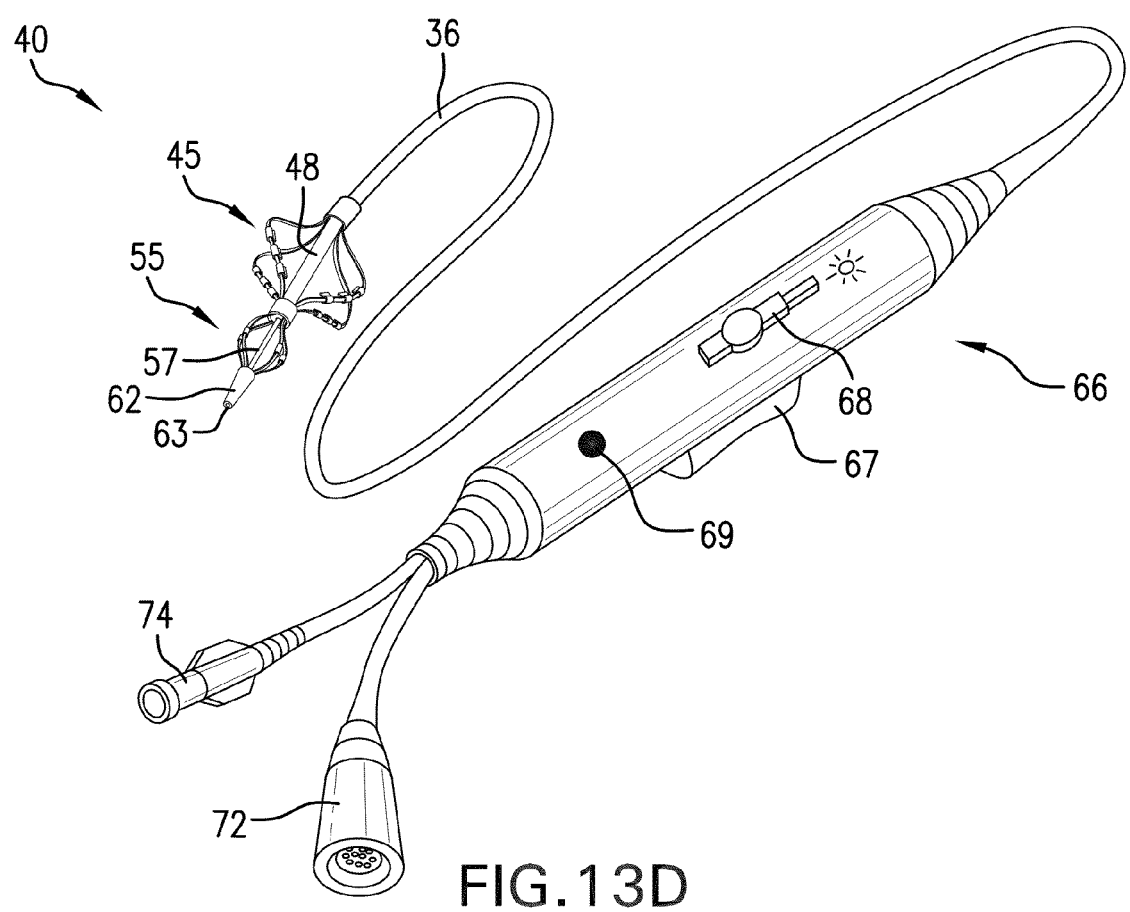

Catheter 40 of FIG. 13C includes on its proximal end, a handle, not shown, but preferably of the type described in reference to FIG. 13(D) and including multiple controls for allowing an operator to: advance and retract first control shaft 48; advance and retract second control shaft 57; activate voltage waveform delivery to one or more of electrodes 46 or 58; operate a user interface of an energy delivery unit or mapping unit (both not shown); or perform another function. The handle includes an exit port through which a guidewire, such as a guidewire that has been placed into a pulmonary vein of the patient, can exit. Carrier assembly 55 is sized such that it can engage the luminal wall of a pulmonary vein, and carrier assembly 45 is sized and of sufficient flexibility such that it can engage the ostium of a pulmonary vein, including a non-circular orifice. Outer shaft 36 is constructed of sufficient material and the handle may be manipulated to apply conforming forces to carrier assembly 55 and/or carrier assembly 45. Both first control shaft 48 and second control shaft 57 are configured to transmit sufficient torque to allow an operator to precisely rotationally position carrier assembly 45 and carrier assembly 55 respectively.

Referring further to FIG. 13(D), catheter 40 is illustrated including the dual carrier assemblies of the catheter of FIG. 13C. Catheter 40 includes a tubular body member, outer shaft 36, which includes on its distal end, proximal carrier assembly 45 and distal carrier assembly 55, as have been described in detail in reference to FIG. 13C. The proximal end of outer shaft 36 is attached to handle 66, which includes multiple controls: slide 67, slide 68 and button 69. Slide 67 is operably attached to first control shaft 48. Slide 68 is operably attached to second control shaft 57. Movement of slides 67 and 68 change the geometries of first carrier assembly 45 and second carrier assembly 55 as has been described in detail in reference to FIG. 13C. Numerous types of mechanical mechanisms can be incorporated into handle 66 to operably advance one or more control shafts, such as linear slides, rotating knobs or rotating levers such as knobs connected to cam assemblies, and other mechanisms used to move the shafts forward and back. Button 69 is used to initiate voltage waveform delivery, such as when first carrier assembly 45 is positioned against a pulmonary vein ostium and catheter 40 is electrically connected to an energy delivery unit, not shown.

Handle 66 includes two pigtails, one which terminates in luer 74 and the other which terminates with electrical connector 72. Luer 74 is in fluid communication with guidewire lumen 63 exiting tip 62 such that catheter 40 can be advanced over-the-wire into the vasculature of the patient. Electrical connector 72 includes multiple connection points for multiple wires that travel within outer shaft 36 and connect to the insulated electrodes and one or more sensors such as temperature sensors included in first carrier assembly 45 and second carrier assembly 55. Electrical connector 72 is configured to electrically connect to one or more of: an energy delivery unit; a mapping unit; an electronic device for receiving and/or transmitting signals and/or power such as signals received from temperature or other physiologic sensors of catheter 40; and combinations of these.

Figure 13E:
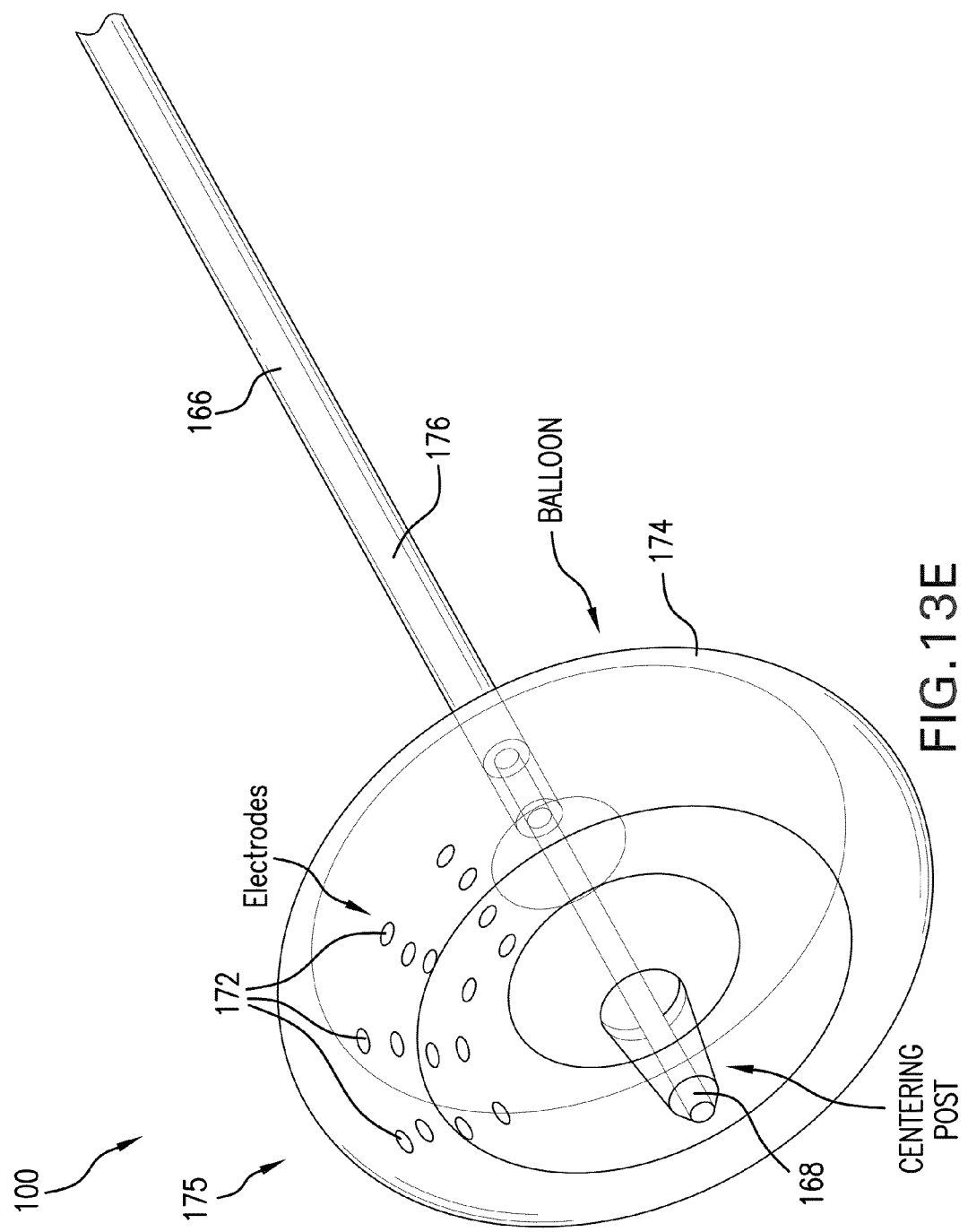

Referring now to FIG. 13E, a catheter of the present disclosure is illustrated in which the carrier assembly includes an inflatable balloon with multiple insulated electrodes mounted on or embedded in its external surface. Catheter 100 includes carrier assembly 175 including balloon 174 and insulated electrodes 172 for delivering electric field to the tissue. Catheter 100 further includes an elongate tubular body, outer shaft 166, which includes an inflation lumen 176 from its proximal portion to the inner cavity of balloon 174. Balloon 174 is sealed and fixedly attached to the distal portion of outer shaft 166. Passage of fluid such as air or saline through the inflation lumen of outer shaft 166 causes balloon 174 to inflate and remain in an expanded state as long as the fluid pressure is maintained. Balloon 174 may be a compliant or non-compliant balloon, and while shown as a disk or donut shape, may have profiles specific to mimic pulmonary vein ostia and the tissue extending therefrom.

Extending from the distal end of and coaxial to external shaft 166 is centering post 168 which traverses from the proximal end to the distal end of balloon 174, and can include a projection configured to engage a pulmonary vein lumen. In a preferred embodiment, a guidewire lumen is included from the distal end to a proximal portion of catheter 100 such that the catheter may be advanced over a guidewire such as a guidewire that has previously been placed into a pulmonary vein ostium or other applicable orifice.

Referring now to FIG. 14, a further embodiment of a catheter (only distal catheter region is illustrated) is presented having a shaft 10 that in turn includes an outer jacket 34, which may be nylon, urethane or other plastic. Outer jacket 34 surrounds stiffener 36, which usually in turn includes a stainless steel braid or coil. The stiffener 36 is disposed about a base layer 38, which preferably comprises a tube of polyimide or other relatively stiff, high durometer material. The stiffness and torqueability characteristics of the shaft can be varied by varying the type of material used for outer jacket 34, stiffener 36 and base layer 38, as well as by using different geometries for the stiffener 38. For example, the stiffener 36 could be a braid or a coil, where the number of filaments, shape of filaments, coiling or weaving pattern, number of turns, and the like, can be varied individually or in combination to provide a desired stiffness. Preferably, the polyimide tube of base layer 38 has a thickness in the range from 0.002 in to 0.005 in.

Outer jacket 34, stiffener 36 and base layer 38 define a central lumen 40 extending the length of shaft 10. Disposed in central lumen 40 are a core wire 42, pull wires 44, electrode wires 46 and, if desired, thermocouple wires 48. Tip section 16 includes tubing 50 of a low durometer flexible plastic, such as Pebax® material, silicone rubber, or other resilient material. Preferably, tip section 16 has a durometer in the range of 30A to 60D. Tubing 50 usually has at least four lumens extending its length in parallel to its longitudinal axis, a central lumen 54 and at least three radially offset lumens 56 (with four being illustrated). Core wire 42 extends through central lumen 54, along with electrode wires 46 and thermocouple wires 48. Pull wires 44 extend from the central lumen of shaft 10 to the radially offset lumens 56 of tip section 16.

A spring tube 58 is also disposed in central lumen 54 of tip section 16, the spring tube 58 fitting snugly against the walls of inner lumen 54 and having a hollow center through which core wire 42, electrode wires 46 and thermocouple wires 48 extend. Spring tube 58 usually comprises a polyimide tube which provides lateral and torsional stiffness as well as kink-resistance to tip section 16. The spring tube 58 could also be a braided or coiled structure, or a composite of multiple layers. Tip section 16 is fixed to shaft 10 at butt joint 18, preferably by heat welding. Central lumen 54 of tip segment 16 is of smaller diameter than central lumen 40 of shaft 10, with spring tube 58 extending a distance, typically about 0.5 in., into the central lumen 40 of shaft 10. Such extension serves to limit kinking at or near butt joint 18 when tip section 16 is deflected. A proximal end 60 of the spring tube 58 will extend into central lumen 40, thereby enhancing the stiffness at the transition between the tip section 16 and the remainder of the shaft 10.

Core wire 42, electrode wires 46 and thermocouple wires 48 extend from central lumen 40 of shaft 10 into central lumen 54 of tip section 16 through the center of spring tube 58. At the distal end of tip section 16, spring tube 58 emerges from central lumen 54 into an aperture 64 within tip electrode 20. Power wire 66 (one of electrode wires 46) is coupled to insulated tip electrode 20 for delivering a time varying electric field. The insulation may be total or partial, as desired, and be applied in any desired pattern (grid, spiral, radial, and the like).

Thermocouple wires 48 terminate in a thermocouple 68 disposed within aperture 64. Preferably, aperture 64 is filled with high temperature adhesive to maintain thermocouple 68 in position. Electrode band wires 70 exit central lumen 54 within spring tube 58 and couple to band electrodes 22. Core wire 42 extends through central lumen 54 into aperture 64 of tip electrode 20.

An electrically and thermally insulating anchor plate 72 is bonded to distal end 74 of tubing 50, tip electrode 20 being bonded to the distal side of anchor plate 72. Anchor plate 72 has a central passage 78 corresponding to central lumen 54 of tip section 16, and four radially offset apertures 76 through which pull wires 44 pass. Pull wires 44 terminate in anchors 80, which usually comprise steel balls formed on or welded to ends of pull wires 44. The anchors 80 are of larger diameter than apertures 76, providing a strong, pivotal connection between pull wires 44 and the distal end of tip section 16. The anchor plate may be formed from any polymeric or ceramic material having the necessary mechanical strength and electrical and thermal insulating properties. Preferred is the use of polyether ether ketone, available from ICI Americas, Inc., Wilmington, Del., under the tradename Victrex.

Figure 15A:
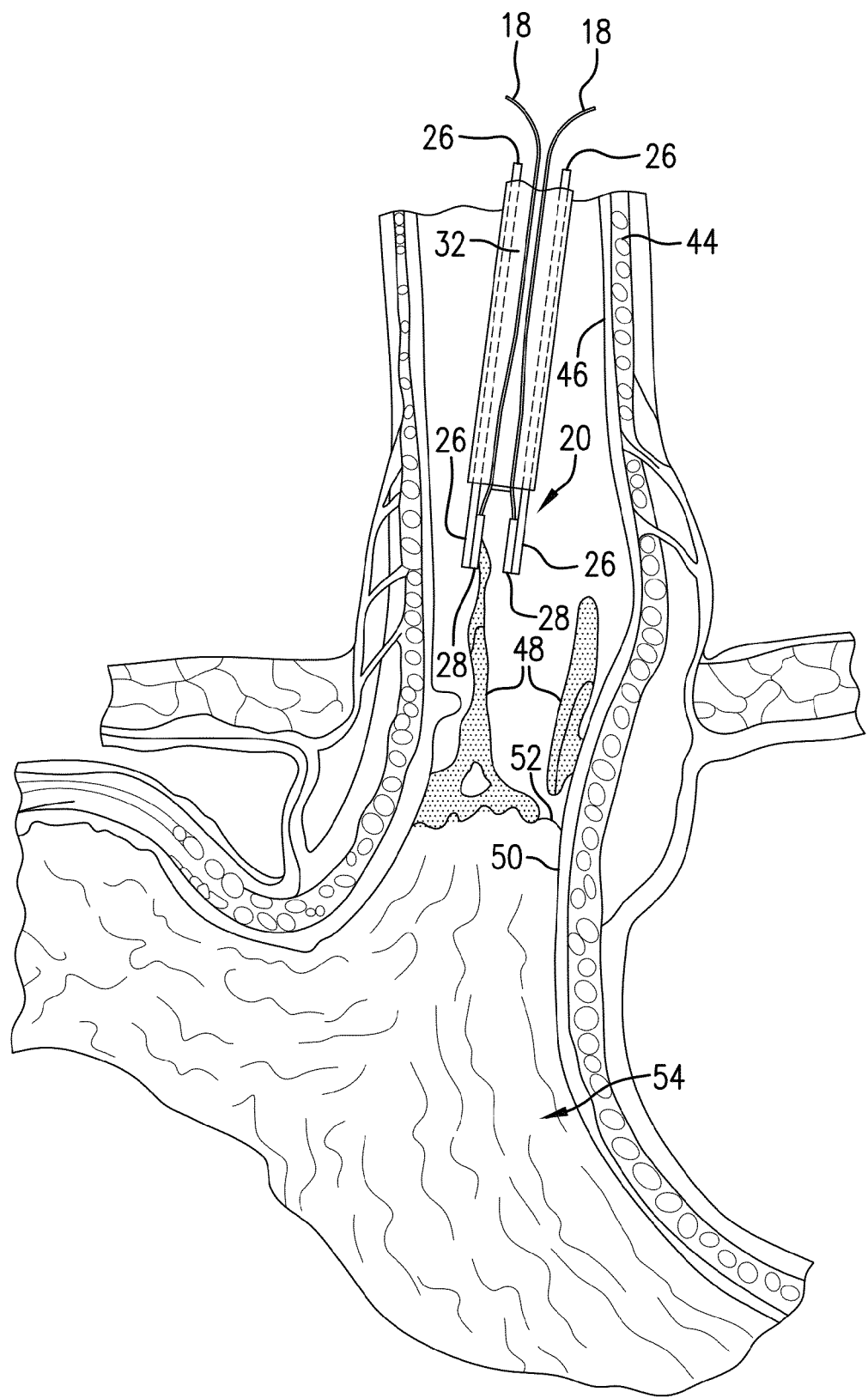
FIGS. 15A-15B illustrate a further treatment device in accordance with the disclosure.
Figure 15B:
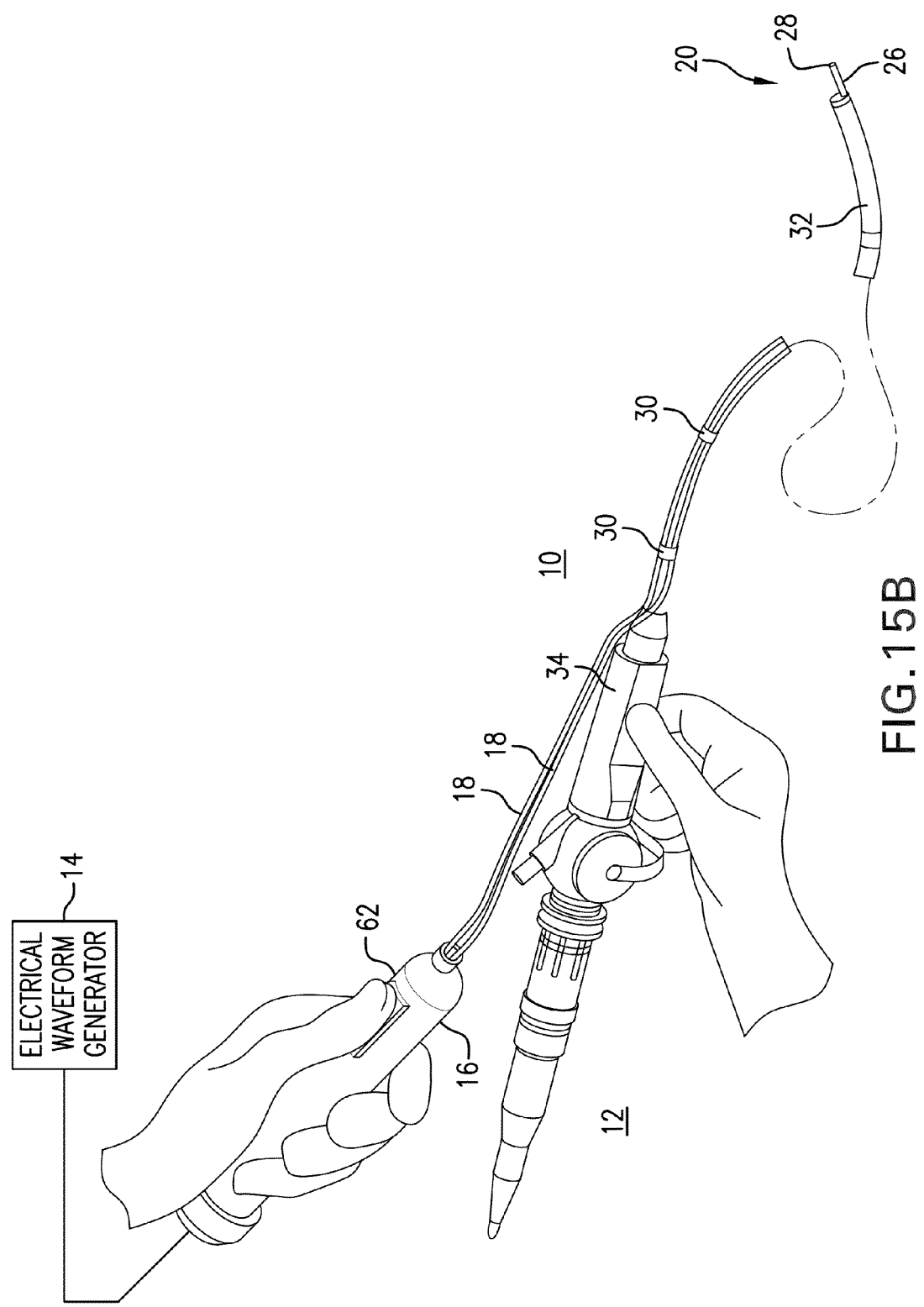

FIGS. 15A-15B illustrate the use of a further embodiment of a catheter to treat diseased tissue 48 in the lower esophagus 42. One embodiment of the system 10 may be mounted on a flexible endoscope 12 (also referred to as endoscope 12). The flexible endoscope 12 includes an endoscope handle 34 and a flexible shaft 32. The endoscopic system 10 generally comprises one or more therapeutic/diagnostic probe 20, a plurality of conductors 18, a handpiece 16 having a switch 62, and an electrical waveform generator 14. The therapeutic/diagnostic probe 20 is located at a distal end of the flexible shaft 32 and the conductors 18 attach to the flexible shaft 32 using a plurality of clips 30. The therapeutic/diagnostic probe 20 comprises an elongate member attached to an electrical energy delivery device comprising one or more insulated electrical therapy electrodes 28. In one embodiment, the therapeutic/diagnostic probe 20 extends through a bore in the flexible shaft 32 such as a working channel 36. In one embodiment, the therapeutic/diagnostic probe 20 may comprise elongate diagnostic probes 26 attached or joined to the electrodes 28 that extend through the working channel 36. In another embodiment, the flexible shaft 32 may comprise two working channels 36 and a first diagnostic probe 26 joined to a first electrode 28 that extends through the distal end of a first working channels 36 and a second diagnostic probe 26 joined to a second electrode 28 that extends through the distal end of a second working channel 36. In one embodiment, the diagnostic probe comprises one or more diagnostic probes 26 attached or joined in any suitable manner to the electrodes 28. For example, the diagnostic probes 26 may be joined or attached to the electrodes 28 by welding, soldering, brazing or other well known techniques. Many different energy sources may be used for welding, soldering, or brazing such as, for example, a gas flame, an electric arc, a laser, an electron beam, friction, and ultrasound. Thus, in one embodiment, the therapeutic/diagnostic probe 20 may be employed in a diagnostic mode to take a biopsy sample of the diseased tissue using the diagnostic probes 26 and, in one embodiment the therapeutic/diagnostic probe 20 may be employed in a therapeutic mode by treating diseased tissue with electric field delivered by the electrodes 28. In other embodiments, the therapeutic/diagnostic probe 20 may be employed in a combination of therapeutic and diagnostic modes. The therapeutic/diagnostic probe 20 may be passed though the one or more working channels 36 located within the flexible shaft 32. The therapeutic/diagnostic probe 20 is delivered to the tissue treatment region endoscopically and is located on top of the diseased tissue to be electrically treated. Once the therapeutic/diagnostic probe 20 is suitably located by the operator, manual operation of the switch 62 on the handpiece 16 electrically connects or disconnects the electrodes 28 to the electrical waveform generator 14. Alternatively, the switch 62 may be mounted on, for example, a foot switch (not shown).

The operator positions the therapeutic/diagnostic probe 20 using endoscopic visualization so that the diseased tissue 48 to be treated is within the field of view of the flexible endoscope 12. Once the operator positions the therapeutic/diagnostic probe 20 such that the insulated electrical therapy electrodes 28 are located above the diseased tissue 48, the operator may energize the insulated electrodes 28 with the electrical waveform generator 14 to apply a strong electric field to the diseased tissue 48 in the tissue treatment region. The electrodes 28 may be energized with microsecond or nanosecond electrical waveforms as described elsewhere herein. In this manner, the diseased tissue 48 in the tissue treatment region may be electroporated and undergo cell death.

Figure 16:
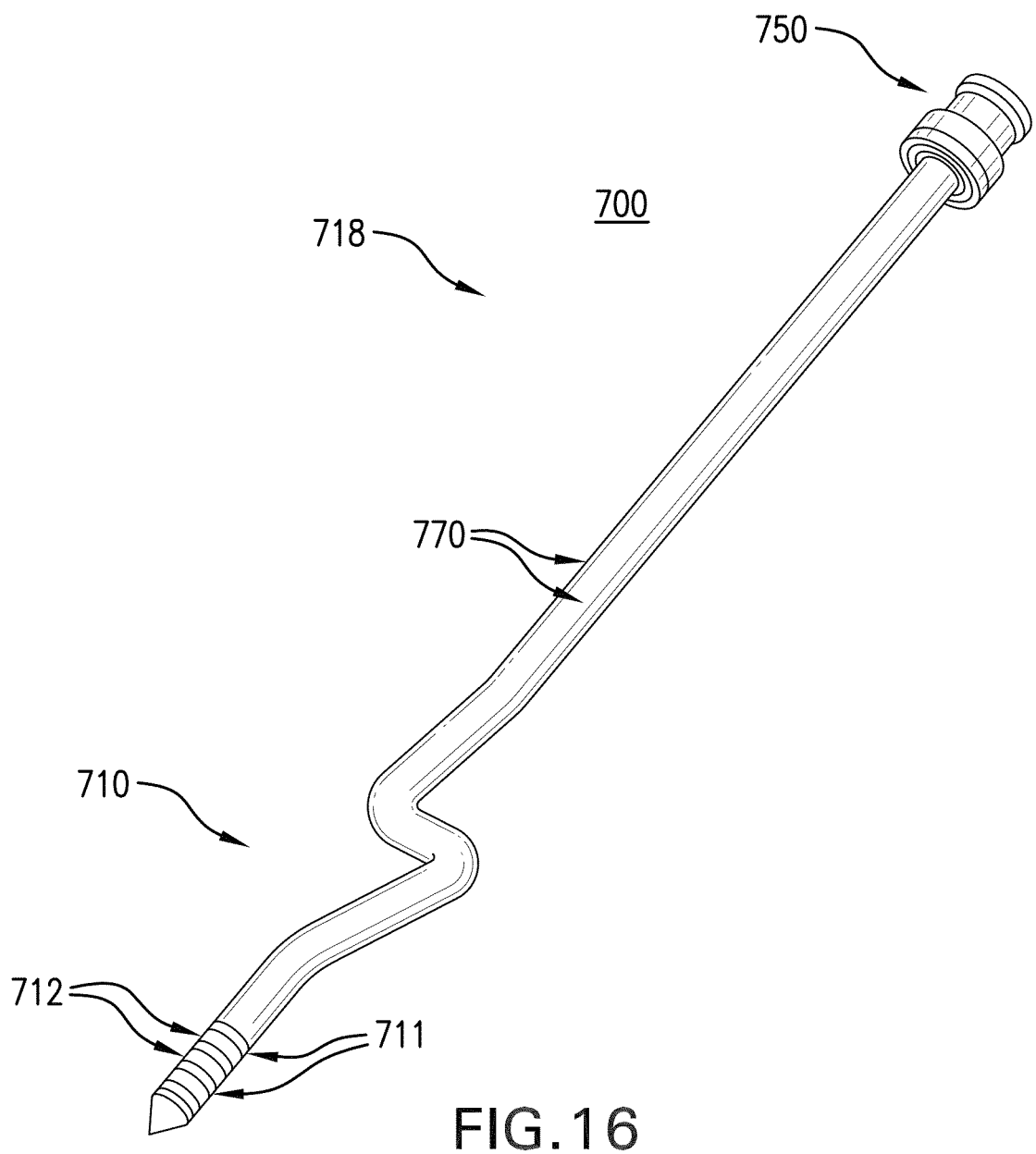
FIG. 16 illustrates still a further treatment device in accordance with the disclosure.

The device 700 illustrated here in FIG. 16 provides a minimally invasive microsurgical tool. Generally, the electrode 700 is a catheter type device with embedded active 712 and ground 711 insulated electrically conductive wires. The electrically conductive wires 711, 712 are annular in shape and are disposed lengthwise along the length of the distal tip 710 of the electrode 700 and may be coated with dielectric material in whole or in part. The insulated conductive wires 711, 712 are spaced a selected distance from one another longitudinally along the length of the electrode 700 and are separated by sections of insulation. The electrode 700 is compatible with existing electroporation electronics and comprises a universal connector 750 for connecting the proximal end 718 of the electrode 700 in operable communication with an electrical pulse generator configured to deliver waveforms as described elsewhere herein. A portion of the electrically conductive wires 711, 712 is encased within the outer body 770 of electrode 700, or electrically conductive leads run from the electrically conductive wires 711, 712 along the length of the electrode 700 from the distal tip 710 to the proximal end 718 for operable communication with an electrical pulse generator. The electrically conductive wires can comprise any type of conducting metal, such as platinum/iridium. Different materials will have different radio-opacity and can be selected according to this characteristic to achieve a particular result. For example, silver is much more radio-opaque than titanium and thus some embodiments of electrodes of the invention can have titanium conductive surfaces/wires, while using silver for the markers.

To ensure biocompatibility, embodiments of the electrode can be sheathed with an insulating polyurethane jacket 770 to enclose the electrically conductive wires leading to the electrical pulse generator. In embodiments, the electrical conducting wires do not need to be entirely conducting. For example, the electrical conductive surfaces can comprise a portion or portions with an insulating coating (especially near their base). The exposed portions or surfaces of the electrically conductive wires 711, 712 on the distal tip 710 can be any thickness and width. Likewise, the amount of separation distance between the electrically conductive wires at the distal tip 710 can be any amount, and the electrodes can comprise any number of conductive wires. In embodiments, the electrodes can be configured in a manner to provide for an adjustable separation distance between electrically conductive wires, and/or an adjustable amount of exposed conductive surface.

The embodiment of FIG. 16 is constructed as a thin device, which allows for easy navigation through the cardiovascular system directly into the treatment site. If desired, the electrode can comprise a J-shaped tip (or similar shape) as is common in angioplasty and catheter-based interventions so as to enable guidance of the electrode through the vasculature to reach the target site. Such an asymmetric tip could also be used as a source for determining rotational orientation for this particular embodiment. Representative dimensions of the electrode device, such as about 0.5 mm in diameter, ensures that it is feasible to be placed in the coronary artery since it is smaller than those already used in catheterization. The diameter or width is thus on the order of 0.5 mm to 1 cm. Preferably, the diameter or width is about 0.5 mm to about 5 mm, such as about 1 mm, 2 mm, 3 mm, or 4 mm. For human use, the device is typically on the order of 40 cm or less in length, such as about 30 cm, 25 cm, or 15 cm, whereas for veterinary use, the length can be much larger, depending on the size of animal to be treated. For treatment of human brain tumors, the length can be on the order of 40 cm.

Figure 17A:
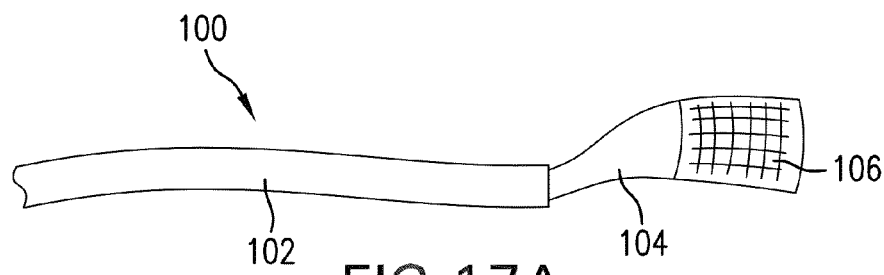
FIGS. 17A-17E illustrate yet further treatment devices in accordance with the disclosure.
Figure 17B:
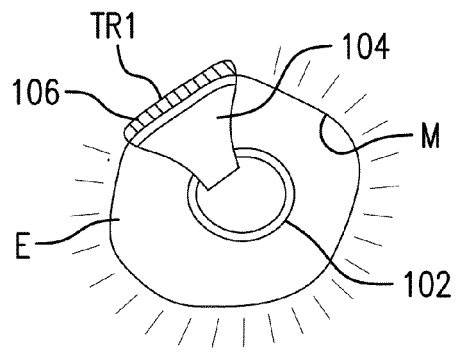
Figure 17C:
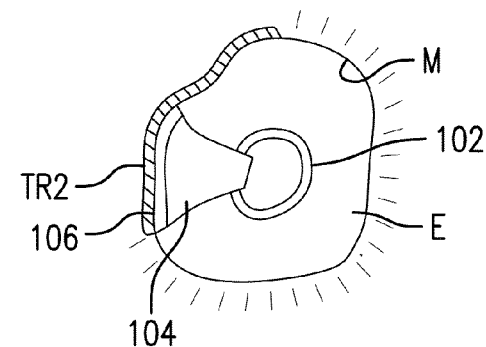
Figure 17D:
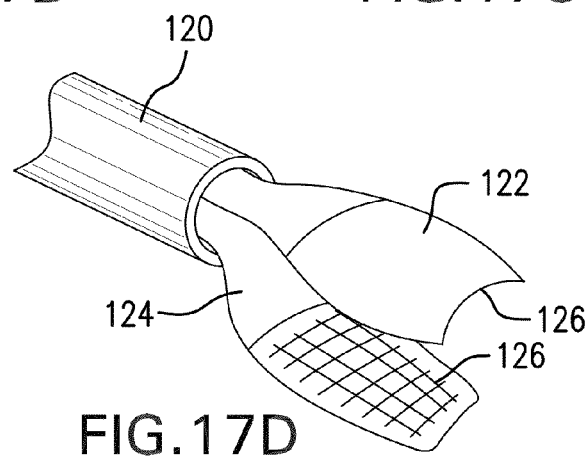

Referring now to FIG. 17A, a catheter 100 comprising an elongated member 102, typically a tubular polymeric extrusion, includes a deployable arcuate electrode delivery structure 104. The structure may be collapsed by drawing it into the tube 102 or deployed by advancing it distally from the tube, as shown in FIG. 17A. A partially or completely insulated electrode array 106 is formed on an outer surface of the arcuate support 104 so that it can be engaged against a circumferential section of the mucosal lining M of the lower esophagus E, as shown in FIG. 17B. After a time varying electric field is applied through the electrode array 106, the arcuate deployment structure 104 may then be rotated so that the electrode array 106 is engaged against a new section of the mucosal wall of the esophagus E. A new region is treated, as shown at $TR_2$ in FIG. 17C. By subsequently rotating the arcuate deployment structure 106, the entire circumferential wall of the esophagus may be treated. It would also be possible to axially reposition the catheter 100 in order to treat successive axial sections of the esophagus as well. Referring now to FIG. 17D, a treatment catheter 120, similar to catheter 100, may be provided with a pair of deployable arcuate structures 122 and 124. Partially/totally insulated arrays of electrodes 126 may be formed on the outer and/or inner surfaces of the deployable arcuate structures. The use of a pair of deployment structures 122 and 124 reduces the total treatment time required when compared to the catheter 100 of FIG. 17A.

Figure 17E:
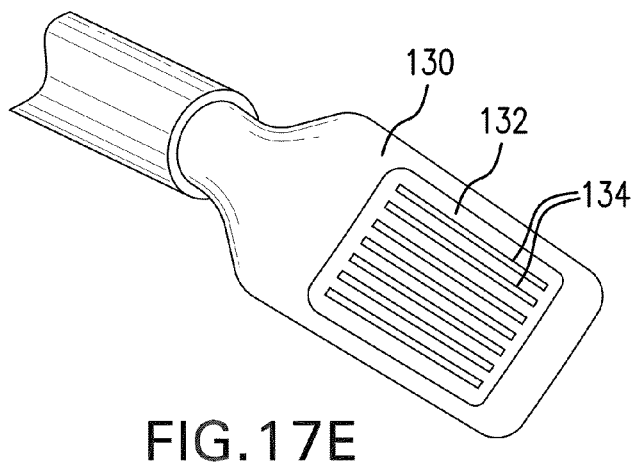

A similar sequential treatment of the mucosal wall of an esophagus may be achieved using an inflatable balloon 130, as shown in FIG. 17E. While most of the balloon 130 is formed from an elastomer, a non-distensible, dimensionally-stable portion 132 is formed as part of the balloon and carries a plurality of partially or completely insulated electrodes 134 spaced-apart in a fixed and dimensionally stable manner. Thus, the elastomeric balloon may be fully inflated in an esophagus and used to treat a circumferential section of the esophagus. After an initial treatment is complete, the balloon may be rotated by a desired amount and used to treat the next circumferential section. Such sequential treatment is continued until the entire circumference of the esophagus has been treated.

Figure 18:
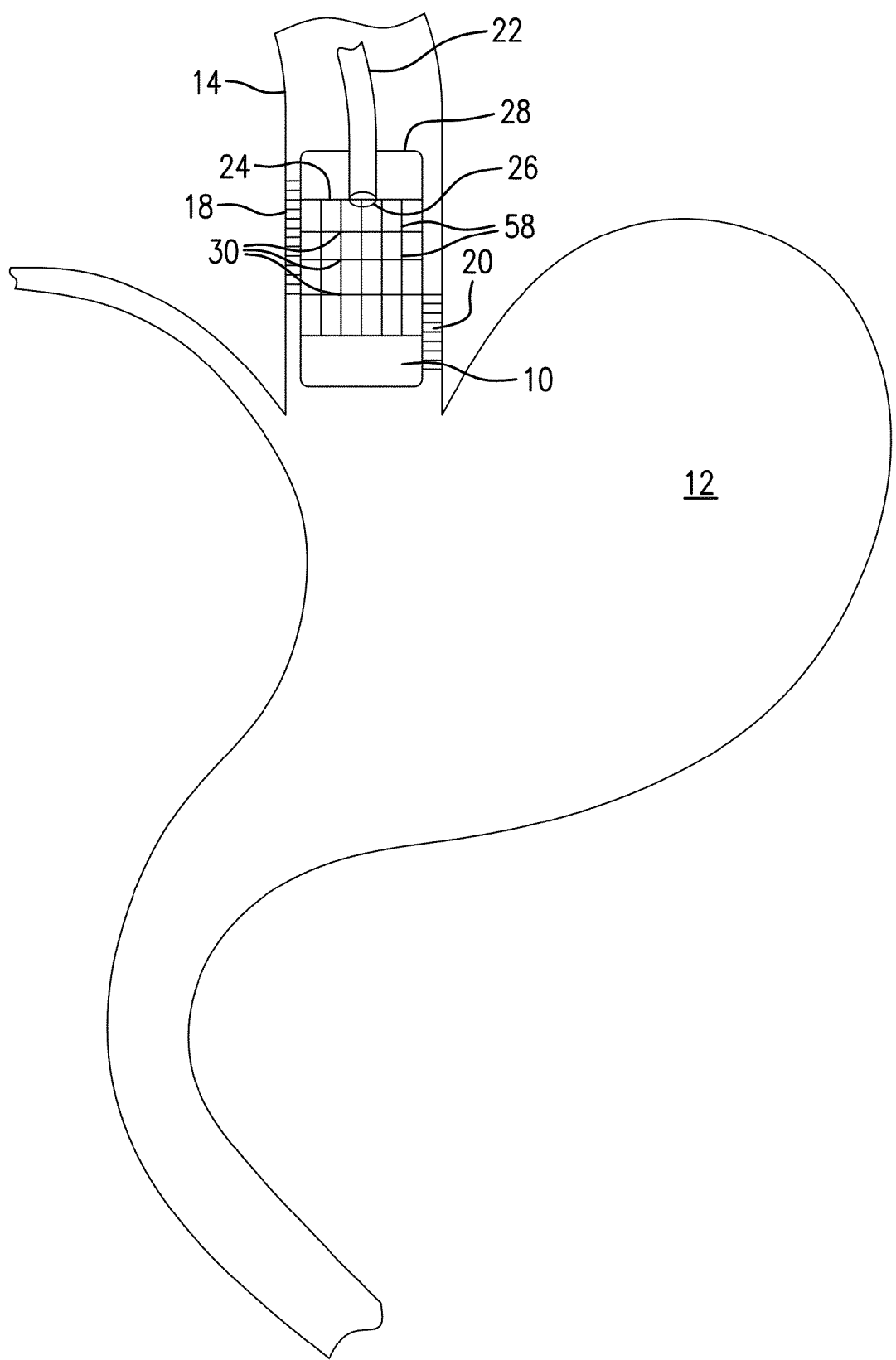
FIG. 18 illustrates a further embodiment of the disclosure.

In accordance with a further embodiment, as illustrated in FIG. 18, a treatment apparatus 10 includes an elongated shaft 22, which can be flexible, that is configured to be inserted into the body in any of various ways selected by the medical provider. Shaft 22 may be placed, (i) endoscopically, e.g. through esophagus 14, (ii) surgically or (iii) by other means. When an endoscope (not shown) is used shaft 22 can be inserted in the lumen of the endoscope, or shaft 22 can be positioned on the outside of the endoscope. Alternately, an endoscope may be used to visualize the pathway that shaft 22 should follow during placement, as well as after removal of the endoscope shaft 22 can be inserted into esophagus 14.

An energy delivery device 24 is provided and can be positioned at a distal end 26 of shaft 22 to provide appropriate energy for electric field application as desired. In various embodiments, energy delivery device 24 is coupled to an energy source as described elsewhere herein for powering energy delivery device 24 at levels appropriate to provide the desired electroporation of tissue. In one embodiment, shaft 22 includes a cable that contains a plurality of electrical conductors surrounded by an electrical insulation layer, with an energy delivery device 24 positioned at distal end 26. A positioning and distending device can be coupled to shaft 22. The positioning and distending device can be configured and sized to contact and expand the walls of the body cavity in which it is placed, by way of example and without limitation, the esophagus. The positioning and distending device can be at different positions of energy delivery device 24, including but not limited to its proximal and/or distal ends, and also at its sides.

Energy delivery device 24 can be supported at a controlled distance from, or in direct contact with the wall of the tissue site. This can be achieved by coupling energy delivery device 24 to an expandable member 28. Suitable expandable members 28 include but are not limited to a balloon, compliant balloon, balloon with a tapered geometry, basket, plurality of struts, an expandable member with a furled and an unfurled state, one or more springs, foam, bladder, backing material that expands to an expanded configuration when unrestrained, and the like. Expandable member 28 can be utilized to regulate and control the amount of energy transferred to the tissue at the tissue site. This can occur with the esophageal wall. Expandable member 28 can be bonded to a portion of shaft 22 at a point spaced from distal end 26. In any embodiment of FIG. 18, the conductive elements can be partially or completely insulated for delivery of the electric field. In another embodiment, expandable member 28 is utilized to deliver the electrical field energy itself. The expandable member can be made of a variety of different materials, including but not limited to an electroconductive elastomer such as a mixture of polymer, elastomer, and electroconductive particles, a nonextensible bladder having a shape and a size in its fully expanded form, which will extend in an appropriate way to the tissue to be contacted.

In another embodiment, an electroconductive member can be formed from an electrically insulating elastomer, with an electroconductive material, such as copper, deposited onto a surface. An electrode pattern can then be etched into the material, and then the electroconductive member can be attached to an outer surface of a balloon. A further partial or total coating of insulating material can then be deposited on top of the electrically conductive material. In one embodiment, the electroconductive member, which can be a balloon 28, has a configuration that is expandable in the shape to conform to the dimensions of the expanded (not collapsed) inner lumen of the tissue site or structure, such as the human lower esophageal tract. In addition, this electroconductive member can include a plurality of electrode area segments 30 that are partially or totally covered by an insulating material.

Figure 19A:
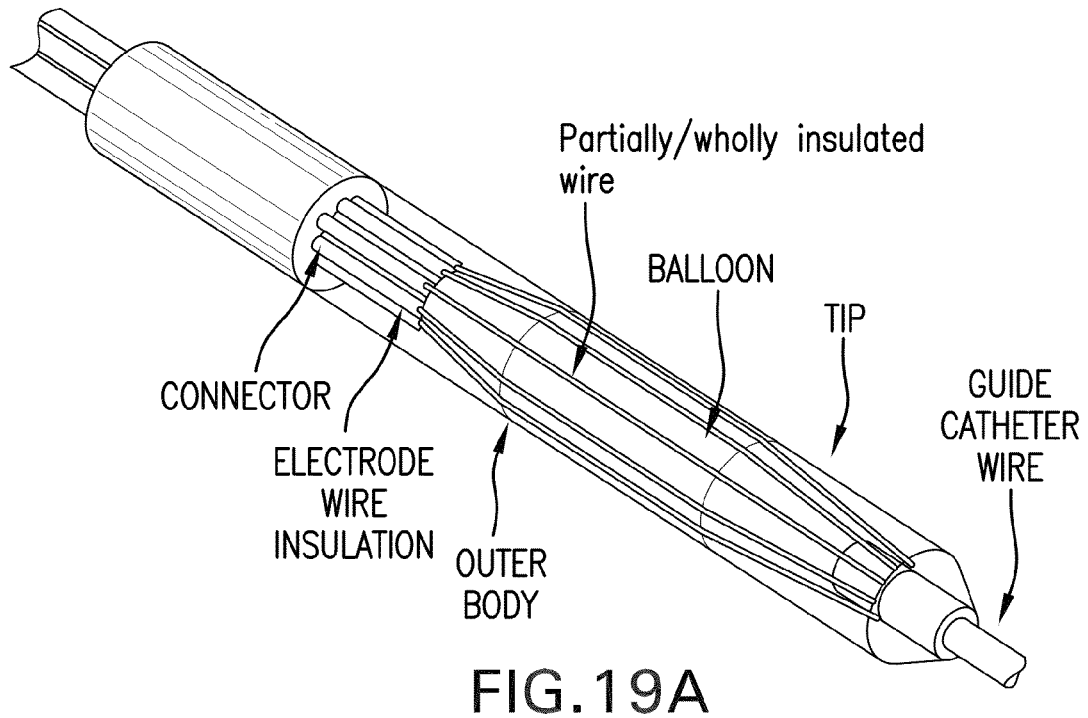
FIGS. 19A-19B illustrate still a further embodiment of the disclosure.
Figure 19B:
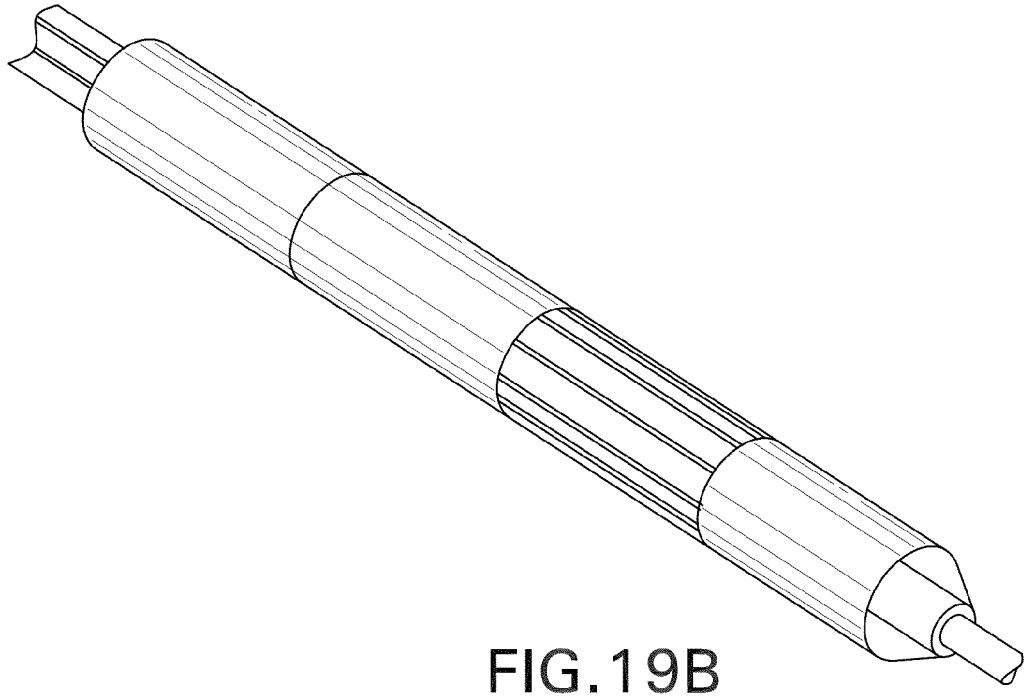

Further exemplary electrodes according to embodiments of the disclosure are shown in FIGS. 19A-19B. Some of the components of the electrode device include a guidewire, tip, outer body, connector, balloon, and partially/wholly insulated conducting wires. The configuration depicted in this embodiment has a 2 mm diameter and is therefore designed for larger coronary vessels, such as the right coronary artery or left main artery, with proximal to medial lumen diameters of roughly 30.6 and 4.3 mm, respectively. See Dodge, J. T., Jr., B. G. Brown, E. L. Bolson, and H. T. Dodge, Lumen diameter of normal human coronary arteries, Influence of age, sex, anatomic variation, and left ventricular hypertrophy or dilation, Circulation, 1992, 86(1): p. 232-46. Such vessels may have typical restenotic lumen diameters of approximately 2.5 mm. See Radke, P. W., A. Kaiser, C. Frost, and U. Sigwart, Outcome after treatment of coronary in-stent restenosis—Results from a systematic review using meta-analysis techniques, European Heart Journal, 2003, 24(3): p. 266-273.

Modern micromachining techniques will allow for the construction of even smaller designs that may target smaller vessels, such as the distal portions and branches of the coronary arteries. Indeed, the devices of the present disclosure may also be scaled up for other applications. Accordingly, the diameter of the outer body of electrodes of the invention can range for example from about 0.1 mm up to about 5 cm. Preferably, electrode embodiments of the invention have an outer diameter ranging from about 0.5 mm to 5 mm, such as from about 1 mm to about 3 mm, such as about 1.5 mm to about 2 mm, or from about 0.75 mm to 3 cm.

In embodiments, the guidewire is the narrowest physical component and is used to direct the surgeon into the appropriate vessel. Although not typical, it can be hollow so that it may be used with a soluble contrast agent used for angiography and fluoroscopy, similar to typical endovascular therapies. See Schwartz, R. S., J. G. Murphy, W. D. Edwards, A. R. Camrud, R. E. Vliestra, and D. R. Holmes, Restenosis after balloon angioplasty, A practical proliferative model in porcine coronary arteries, Circulation, 1990, 82(6): p. 2190-200. The guidewire is usually of a smaller diameter than the diameter of the outer body of the balloon.

The guidewire or catheter forms the support for which all other components of the device are arranged. Over a portion of the catheter between the distal tip and the proximal end of the device is disposed an inflatable balloon. The balloon is secured to the catheter at the distal and proximal ends of the device. An inflation mechanism for providing a fluid into the area between the balloon and catheter is also provided. The balloon can be inflated during use with any inert fluid, such as saline, contrast fluid, air, or even low electrical conductivity sucrose solution. In embodiments where the electrically conductive wires are disposed on the inside of the balloon (between the balloon and the catheter) and where there is present a highly conductive fluid in the lumen (inside the balloon), the flow of the current would be preferentially through the fluid rather than through the wires which may result in a more diffuse electrical field. In preferred embodiments, a low-conductivity buffer is preferred as the fluid to inflate the balloon to more accurately treat target tissue.

The wholly/partially insulated conductive wires or electrodes provide for delivering the time varying voltage waveform to apply an electric field target tissue from an electrical pulse generator. During use of the device, proximal ends of the wires/electrodes are in operable communication with a pulse generator. The wires can be hardwired directly to the pulse generator, or in preferred embodiments the electrode is equipped with a universal connector (or other connecting structure) for securing the electrically conductive wires/electrodes to the electrical pulse generator in an operably connective manner. For electrodes having a greater number of electrically conductive wires than the number of outputs available on a pulse generator it is desired to be used with, the electrodes and or pulse generator can be retrofitted or adapted accordingly to operably cooperate with one another. In embodiments, when there are more conductive wires on the electrode, e.g., 8 wires, than there are outputs on the pulse generator, e.g., 6 outputs, systems of the invention can comprise an electrode-generator interface that cooperates with the generator to switch which wires are active for a given pulse set in the overall sequence. More specifically, the interface can comprise a switch for switching between wires 4 and 8 for an 8-electrode system, since those wires would be least likely to be energized at the same time at 180 degrees apart. Other examples for operation of an interface for treatments using basic 2-at-a-time pulsing pairs, the system can be connected to all 8 wires on the output, and just have a positive and negative input to take from the generator, where it would automatically switch pairs 1-2 to 2-3 and so on, while the generator's positive and negative outputs (port 1 and 2) would change pulse set 1 at (ex.) 2000 V (wires 1-2), then change to 1500 V (wires 2-3) for the second.

In this embodiment, the electrically conductive wires are elongated and are disposed along the length of the balloon. The wires are spaced a selected distance from one another around the circumference of the electrode. In FIGS. 19A-19B, there are eight electrically conductive wires/electrodes circumferentially spaced around the balloon. The distal ends and proximal ends of the electrically conductive wires/electrodes are protected or encased by a relatively thick outer insulative body, while a medial portion of the wires/electrodes to be placed against the anatomical region of interest includes a relatively thinner insulating layer, or is partially uninsulated and directly exposed to the atmosphere or vessel wall when in use.

The distal tip of the balloon preferably includes a conical distal end to allow easy advancement through the vessel lumen. The conical distal end is preferably formed from or is in operable communication with a portion of the outer body of the device. The outer body of the device is an insulative encasing providing protection for the components of the device and for controlling the amount of exposure of the electrically conductive wires. Another portion of the outer body of the device provides for a proximal encasing disposed at the proximal end of the electrode. In embodiments, there is a gap or separation distance between the distal and proximal encasings or portions of the outer body. This gap or unprotected area of the electrode exposes the electrically conductive wires to the atmosphere.

A connector is disposed proximally of the balloon. The connector is hollow to allow movement with respect to the guidewire, and has an internal chamber that extends all the way back to the proximal ends of the balloon catheter that can carry fluids, such as physiologic saline or air or low electrical conductivity sucrose solution.

The balloon is attached to the connector. Running through the body/connector assembly is an array of 8 conducting 35 gauge wires (0.15 mm). These wires are insulated throughout the electrode apparatus until they reach the highly insulative balloon, after which they are exposed. In embodiments, the conducting wires can be attached to the proximal portion of the connector, but their distal ends are free and enclosed within the casing of the tip. This allows free expansion of the wires with inflation of the balloon. In other embodiments, the wires can be attached to the surface of the balloon and/or the distal ends of the wires attached to the distal tip, or distal outer body, or distal portion of the connector of the electrode.

Thus, in some illustrative embodiments, the disclosure provides:

1. A method for generation of a time-varying electric field within living tissue of animal or human body wherein the time variation of the field takes the form of a pulse having a rise and fall time lasting between about 1-100 microseconds and lasting between about 2-200 microseconds (or any increment of one microsecond therebetween) and having a peak magnitude of 100-100,000 V/cm (or any increment of 1.0 V/cm therebetween), wherein a pulsed or oscillating voltage of about the same duration is applied between conducting electrodes. At least one electrode is placed in the vicinity of the tissue, while conduction current from the electrode(s) into the tissue is substantially reduced or prevented by the presence of a dielectric insulator surrounding the electrodes. The peak value of the electric field within the tissue at the anatomical region of interest is controlled by the rate of voltage variation and by the peak voltage imposed by the electrical signal generator. An electrical current limiting barrier layer is configured to be disposed between the at least one electrode and the anatomical region of interest.

2. A method for generation of a time-varying electric field within living tissue of animal or human body wherein the time variation of the field takes the form of a pulse having a rise and fall time lasting between about 1-100 nanoseconds and lasting between about 2-200 nanoseconds (or any increment of one nanosecond therebetween) and having a peak magnitude of 100-100,000 V/cm (or any increment of 1.0 V/cm therebetween), wherein a pulsed or oscillating voltage of about the same duration is applied between conducting electrodes. At least one electrode is placed in the vicinity of the tissue, while conduction current from the electrode(s) into the tissue is substantially reduced or prevented by the presence of a dielectric insulator surrounding the electrodes. The peak value of the electric field within the tissue at the anatomical region of interest is controlled by the rate of voltage variation and by the peak voltage imposed by the electrical signal generator. An electrical current limiting barrier layer is configured to be disposed between the at least one electrode and the anatomical region of interest.

3. A device for generation of a time-varying electric field within living tissue of animal or human body wherein the time variation of the field takes the form of a pulse having a rise and fall time lasting between about 1-100 microseconds (or any increment of one microsecond therebetween) and lasting between about 2-200 microseconds and having a peak magnitude of 100-100,000 V/cm (or any increment of 1.0 V/cm therebetween), wherein a pulsed or oscillating voltage of about the same duration is applied between conducting electrodes. At least one electrode is placed in the vicinity of the tissue, while conduction current from the electrode(s) into the tissue is substantially reduced or prevented by the presence of a dielectric insulator surrounding the electrodes. The peak value of the electric field within the tissue at the anatomical region of interest is controlled by the rate of voltage variation and by the peak voltage imposed by the electrical signal generator. An electrical current limiting barrier layer is configured to be disposed between the at least one electrode and the anatomical region of interest.

4. A device for generation of a time-varying electric field within living tissue of animal or human body wherein the time variation of the field takes the form of a pulse having a rise and fall time lasting between about 1-1000 nanoseconds (or any increment of one nanosecond therebetween) and lasting between about 2-2000 nanoseconds and having a peak magnitude of 100-100,000 V/cm (or any increment of 1.0 V/cm therebetween), wherein a pulsed or oscillating voltage of about the same duration is applied between conducting electrodes. At least one electrode is placed in the vicinity of the tissue, while conduction current from the electrode(s) into the tissue is substantially reduced or prevented by the presence of a dielectric insulator surrounding the electrodes. The peak value of the electric field within the tissue at the anatomical region of interest is controlled by the rate of voltage variation and by the peak voltage imposed by the electrical signal generator. An electrical current limiting barrier layer is configured to be disposed between the at least one electrode and the anatomical region of interest.

All statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Descriptions herein of circuitry and method steps and represent conceptual embodiments of illustrative circuitry and software embodying the principles of the disclosed embodiments. Thus the functions of the various elements shown and described herein may be provided through the use of dedicated hardware as well as hardware capable of executing software in association with appropriate software as set forth herein.

In the disclosure hereof any element expressed as a means for performing a specified function is intended to encompass any way of performing that function including, for example, a) a combination of circuit elements and associated hardware which perform that function or b) software in any form, including, therefore, firmware, microcode or the like as set forth herein, combined with appropriate circuitry for executing that software to perform the function. Applicant thus regard any means which can provide those functionalities as equivalent to those shown herein.

Similarly, it will be appreciated that the system and process flows described herein represent various processes which may be substantially represented in computer-readable media and so executed by a computer or processor, whether or not such computer or processor is explicitly shown. Moreover, the various processes can be understood as representing not only processing and/or other functions but, alternatively, as blocks of program code that carry out such processing or functions.

The methods, systems, computer programs and mobile devices of the present disclosure, as described above and shown in the drawings, among other things, provide for improved methods, systems and machine readable programs for carrying out therapeutic treatments. It will be apparent to those skilled in the art that various modifications and variations can be made in the devices, methods, software programs and mobile devices of the present disclosure without departing from the spirit or scope of the disclosure. Thus, it is intended that the present disclosure include modifications and variations that are within the scope of the subject disclosure and equivalents. All documents referenced herein are expressly incorporated by reference herein in their entireties for any purpose whatsoever.

What is claimed is:

1. A system for treating a region of living tissue, comprising:
   a) an electrical signal generator configured to generate a time-varying electric field having a plurality of pulses, each of said plurality of pulses having a rise time and a fall time, wherein at least one of the rise time and the fall time lasts between about 1-100 microseconds and wherein the rise time and the fall time lasts for a total duration between about 2-200 microseconds in combination;
   b) at least one electrode configured to be placed proximate an anatomical region of interest to deliver the time varying electric field to the anatomical region of interest, wherein the electric field has a peak magnitude between about of 100-100,000 V/cm, and wherein the peak value of the electric field within tissue at the anatomical region of interest is controlled by the rate of voltage variation and by the peak voltage imposed by the electrical signal generator; and c) an electrical current limiting barrier layer configured to be disposed between the at least one electrode and the anatomical region of interest.

2. A system for treating a region of living tissue, comprising:

a) an electrical signal generator configured to generate a time-varying electric field having a plurality of pulses, each of said plurality of pulses having a rise time and a fall time, wherein at least one of the rise time and the fall time lasts between about 1-1000 nanoseconds and wherein the rise and fall time lasts for a total duration between about 2-2000 nanoseconds in combination;

b) at least one electrode configured to be placed proximate an anatomical region of interest to deliver the time varying electric field to the anatomical region of interest, wherein the electric field has a peak magnitude between about 100-100,000 V/cm, and wherein the peak value of the electric field within tissue at the anatomical region of interest is controlled by the rate of voltage variation and by the peak voltage imposed by the electrical signal generator; and c) an electrical current limiting barrier layer configured to be disposed between the at least one electrode and the anatomical region of interest.

3. The system of claim 1 or 2, wherein the electrical current limiting barrier includes an insulating material between about 1-2000 micrometers in thickness.

4. The system of claim 1 or 2, wherein the electrical current limiting barrier includes a gas filled gap that begins to conduct electrical current therethrough when the electric field across the gas filled gap exceeds the ionization threshold of gas within the gas filled gap.

5. The system of claim 1 or 2, wherein the electrical current limiting barrier includes an ionic conducting liquid or polymer.

6. The system of claim 1 or 2, wherein the at least one electrode is configured to apply an electric field to the anatomical region of interest that is oriented in a direction that is predominantly normal to the said electrode within the anatomical region of interest.

7. The system of claim 1 or 2, wherein the at least one electrode is configured to apply an electric field to the anatomical region of interest that is oriented in a direction that is predominantly tangential to the said electrode within the anatomical region of interest.

8. The system of claim 1 or 2, wherein the at least one electrode is formed proximate a surface of an inflatable member that can be selectively inflated to bring the at least one electrode into proximity of the anatomical region of interest.

9. The system of claim 1 or 2, wherein the at least one electrode is patterned, the patterning being defined by alternating regions of exposed conductor and insulating material, or alternating regions of insulating material of differing thicknesses.

10. The system of claim 1 or 2, wherein the at least one electrode is flexible.

11. The system of claim 1 or 2, wherein the at least one electrode is resilient.

12. The system of claim 1 or 2, wherein the at least one electrode includes a plurality of elongate conductors surrounding a central axis that can be deployed radially outwardly from the central axis.

13. The system of claim 12, wherein the plurality of elongate conductors include an insulating layer along substantially their entire length.

14. The system of claim 13, wherein the thickness of the insulating layer changes along the length of the plurality of elongate conductors.

15. The system of claim 14, wherein the thickness of the insulating layer is less along a portion of the plurality of elongate conductors that is configured to be placed proximate the anatomical region of interest.

16. The system of claim 12, wherein the plurality of elongate conductors are partially insulated along a portion of the plurality of elongate conductors that is configured to be placed proximate the anatomical region of interest.

17. A method comprising applying an electric field to the anatomical region of interest using a system according to claim 1.

18. The method of claim 17, wherein the anatomical region of interest is exposed to the electric field for between about one tenth of a second and about one hour.

19. The method of claim 17, wherein the anatomical region of interest is exposed to the electric field for between about five seconds and about twenty minutes.

20. The method of claim 17, wherein the anatomical region of interest is exposed to the electric field for between about thirty seconds and about ten minutes.

21. The method of claim 17, wherein the anatomical region of interest is exposed to the electric field for between about three minutes and about seven minutes.

22. The method of claim 17, wherein the anatomical region of interest is on or in an animal.

* * * * *